(12) United States Patent
Goldstein et al.

(10) Patent No.: US 7,297,326 B2
(45) Date of Patent: Nov. 20, 2007

(54) OCULAR DIAGNOSIS OF ALZHEIMER'S DISEASE

(75) Inventors: Lee E. Goldstein, Marblehead, MA (US); Leo T. Chylack, Jr., Duxbury, MA (US)

(73) Assignees: The General Hospital Corporation, Boston, MA (US); The Brigham and Women's Hospital, Inc., Boston, MA (US)

( * ) Notice: Subject to any disclaimer, the term of this patent is extended or adjusted under 35 U.S.C. 154(b) by 557 days.

(21) Appl. No.: 10/715,776

(22) Filed: Nov. 18, 2003

(65) Prior Publication Data

US 2004/0152068 A1 Aug. 5, 2004

Related U.S. Application Data

(63) Continuation-in-part of application No. 10/132,779, filed on Apr. 25, 2002, now Pat. No. 6,849,249, and a continuation-in-part of application No. 09/935,126, filed on Aug. 21, 2001, now Pat. No. 7,107,092.

(60) Provisional application No. 60/452,336, filed on Mar. 5, 2003, provisional application No. 60/427,153, filed on Nov. 18, 2002, provisional application No. 60/287,124, filed on Apr. 27, 2001, provisional application No. 60/226,590, filed on Aug. 21, 2000.

(51) Int. Cl.
A61K 49/00 (2006.01)
(52) U.S. Cl. .................. 424/9.1; 424/9.6; 424/9.61
(58) Field of Classification Search ............... 424/1.11, 424/9.1, 9.3, 9.6, 9.61; 548/156
See application file for complete search history.

(56) References Cited

U.S. PATENT DOCUMENTS

| | | | |
|---|---|---|---|
| 5,540,226 A | 7/1996 | Thurston et al. ............ 128/633 |
| 5,571,671 A * | 11/1996 | Potter ........................... 435/6 |
| 5,973,779 A | 10/1999 | Ansari et al. ................ 356/301 |
| 6,001,331 A | 12/1999 | Caprathe et al. ............. 424/9.1 |
| 6,013,034 A | 1/2000 | Da Cunha Vaz et al. ... 600/310 |
| 6,054,114 A | 4/2000 | Lansbury, Jr. et al. ..... 424/1.11 |
| 6,114,175 A | 9/2000 | Klunk et al. ............ 514/230.5 |
| 6,133,259 A | 10/2000 | Klunk et al. .................. 436/63 |
| 6,168,776 B1 | 1/2001 | Klunk et al. ................ 424/1.11 |
| 6,198,532 B1 | 3/2001 | Cabib et al. ................. 356/346 |
| 6,423,270 B1 | 7/2002 | Wall ............................ 422/61 |
| 6,849,249 B2 * | 2/2005 | Goldstein et al. ........... 424/9.1 |
| 2002/0133019 A1 * | 9/2002 | Klunk et al. ................ 548/156 |

FOREIGN PATENT DOCUMENTS

CA 2272320 5/1998
CA 2301142 2/1999

WO WO98/22146 5/1998

OTHER PUBLICATIONS

Ansari, et al., *Diabetes Technol. Ther.*, 1(2):159-168 (1999).
Ansari, et al., *J. Crystal Growth*, 168:216-226 (1996).
Atwood, et al., *J. Biol. Chem.*, 273:(21):12817-12826 (1998).
Bacskai, et al., *J. Cereb. Blood Flow &Metabol.*, 22(9):1035-1041 (2002).
Berk, et al., *Ophthalmic Genetics*, 17(1):15-19 (1996).
Blacker, et al., *Archives of Neurology*, 55(3):294-296 (1998).
Bloemendal, H., *Invest. Ophthalmol. Vis. Sci.*, 32(3):445-455 (1991).
Borchelt, et al., *Neuron*, 17:1005-1013 (1996).
Brás, et al., *Ophthalmic Paediatrics and Genetics*, 10(4): 271-277 (1989).
Bron, et al., *Ophthalologica*, 214:86-104 (2000).
Burggren, et al., *Curr. Top. Medic. Chem.*, 2:385-393 (2002).
Bush, A. I., *Curr. Opin. Chem. Biol.*, 4:184-191 (2000).
Cai, et al., *Science*, 259:514-516 (1993).
Chartier-Harlin, et al., *Nature*, 353:844-846 (1991).
Christie, et al., *J. Neurosci.*, 21(3):858-864 (2001).
Chylack, et al., *Invest. Ophtalmol. Vis. Sci.*, 24:424-431 (1983).
Citron, et al., *Nature*, 360:672-674 (1992).
Cuajungco, et al., *J. Biol. Chem.*, 275(26):19439-19442 (2000).
da Cunha, et al., *Am. J. Ophthalmol.*, 122:236-244 (1996).
Duff, et al., *Nature*, 383:710-713 (1996).
Ernst, et al., *Am. J. Pub. Health*, 84(8):1261-1264 (1994).
Esch. et al., *Science*, 248:1122-1124 (1990).
Frederikse, P. H., *Curr. Eye Res,.* 20(6):462-468 (2000).
Frederikse, et al., *Curr. Eye Res.*, 17:947-952 (1998).
Frederikse, et al., *Invest. Ophthalmol. Vis. Sci.*, 41:S627, Abstract No.: 3330-B428, (2000).
Frederikse, et al., *J. Biol. Chem.*, 271(17):10169-10174 (1996).
Glenner, et al., *Biochem. Biophys. Rev. Commun.*, 120(3):885-890 (1984).
Goate, et al., *Nature*, 349:704-706 (1991).
Goldgaber, et al., *Science*, 235:877-880 (1987).
Haass, et al., *Nature*, 359:322-325 (1992).
Hankinson, S. E., in *Principles and Practice of Ophthalmology*, D. M. Albert and F. A. Jakobiec, editors, Philadelphia, PA, W. B. Saunders, Co., pp. 1255-1265 (1994).
Hanlon, et al., *Phys. Med. Biol.*, 45: R1-R59 (2000).

(Continued)

Primary Examiner—Michael G. Hartley
Assistant Examiner—Samala Jagadishwar
(74) Attorney, Agent, or Firm—Mintz, Levin, Cohn, Ferris, Glovsky and Popeo, P.C.; Ingrid A. Beattie

(57) ABSTRACT

The invention features a method of diagnosing or providing a prognosis regarding the state of Alzheimer's Disease in a mammal by contacting an ocular tissue with a detectably-labeled compound, which binds to an amyloid protein. An increase in binding of the compound to the ocular tissue compared to a normal control level of binding indicates that the mammal is suffering from or is at risk of developing Alzheimer's Disease.

11 Claims, 8 Drawing Sheets

OTHER PUBLICATIONS

Harding, J. J., *Alzheimer Disease and Associated Disorders*, 11(3):123 (1997).
Harding, J. J., *Curr. Opin. Ophthalmol.*, 9:10-13 (1998).
Helmuth, L., *Science*, 297:752-753 (2002).
Hendricks, et al., *Nature Genet.*, 1:218-221 (1992).
Hendrie, H. C., *Am. J. Geriatr. Psychiatry*, 6(2): S3-S18 (1998).
Hsiao, et al., *Science*, 274:99-102 (1996).
Huang, et al., *Biochemistry*, 38(24):7609-7616 (1999).
Huang, et al., *J. Biol. Chem.*, 272(42):26464-26470 (1997).
Huang, et al., *J. Biol. Chem.*, 274(52):37111-37116 (1999).
Huang, et al., *J. Nutr.*, 130:1488S-1492S (2000).
Kang et al., *Nature*, 325:733-736 (1987).
Kauffman, et al., *Pediatrics*, 86(5):797-798 (1990).
Klunk, et al., *Neurobiol. Aging*, 15(6):691-698 (1994).
Klunk, et al., *J. Neuropathol. Exp. Neurol.*, 61(9):797-805 (2000).
Klunk, et al., *J Neurosci.*, 23(6):2086-2092 (2003).
Klunk, et al., *Life Sci.*, 69:1471-1484 (2001).
Kung, et al., *Brain Res.*, 956:202-210 (2002).
Kung, et al., *J. Mol. Neurosci.*, 19:7-10 (2002).
Lee, et al., *J. Med. Chem.*, 44:2270-2275 (2001).
Leske, et al., *Ophthalmology*, 105: 831-836 (1998).
Levy, et al., *Science*, 248:1124-1126 (1990).
Lewis, R., *The Scientist*, vol. 16, 3 pgs., (2002).
Link, et al., *Neurobiol. Aging*, 22(2):217-226, 2001.
Lott, I. T., *Annals of the New York Academy of Sciences*, 396:15-27 (1982).
Lott, I. T., *Prog. Clin. Biol. Res.*, 379: 1-14 (1992).
Lovell, et al., *J. Neurol. Sci.*, 158(1):47-52 (1998).
Markesbery, et al., *Alzheimer Disease*, R. D. Terry, R. Katzman, K.L. Bick and S.S. Sisodia, editors, New York, Libbincott Williams and Wilkins, Chapter 27, pp. 401-414 (1999).
Masters, et al., *Proc. Natl. Acad. Sci. USA*, 82:4254-4249 (1985).
Masters, et al., *EMBO J.*, 4(11): 2757-2763 (1985).
Mathis, et al., *Biorganic & Medic. Chem. Lett.*, 12:295-298 (2002).
McLellan, et al., *J. Neurosci.*, 23(6):2212-2217 (2003).
Miura, et al., *Biochemistry*, 38:11560-11569 (1999).
Miura, et al., *Biochemistry*, 39:7024-7031 (2000).
Mullan et al., *Nature Genet.*, 1:345-347 (1992).
Murrell et al., *Science*, 254:97-99 (1991).
Oyama, et al., *J. Neurochem.*, 62:1062-1066 (1994).
Pappolla, et al., *Am. J. Pathol.*, 152(4):871-877 (1998).
Pettergrew, et al., *Neurobiol. Aging*, 16(1):1-4 (1995).
Pueschel, S. M., *Am. J. Med. Genetics*, Supp. 7:52-56 (1990).
Robakis, et al., *Proc. Natl. Acad. Sci. USA*, 84:4190-4194 (1987).
Roher, et al., *J. Neurochem.*, 61:1916-1926 (1993).
Sano, et al., *N. E. J. Med.*, 336(17):1216-1222 (1997).
Scheuner, et al., *Nat. Med.*, 2(8):864-870 (1996).
Selkoe, D.J., *Annal. N. Y. Acad. Sci.*, 924:17-25, 2000.
Seubert, et al., *Nature*,359:325-327 (1992).
Shoji, et al., *Science*, 258:126-129 (1992).
Siik, et al., *Acta Ophtamol.*, (Cophen) 71(3):388-392 (1993).
Siik, et al., *Acta Ophtamol.*, (Scand.) 75(5):524-527, 1997.
Siik, et al., *Acta Ophtamol.*, (Scand.) 77(5):509-514, 1999.
Siik, et al, *Acta Ophtamol.*, (Copen) 69(2):187-192 (1991).
Siik, et al, Acta Ophtamol., (Copen) 70(3):383-388 (1992).
Skovronsky, et al., *Proc. Natl. Acad. Sci. USA*, 97(13):7609-7614 (2000).
Smith, et al., *J. Neurochem.*, 70:2212-2215 (1998).
Spector, A., *FASEB J.*, 9:1173-1182 (1995).
St. George-Hyslop, P. H., *Biol. Psychiatry*, 47:183-199 (2000).
Stark, et al., *Arch. Ophthalmol.*, 107:1441-1444 (1989).
Styren, et al., *J. Histochem. Cytochem.*, 48(9):1223-1232 (2002).
Suzuki, et al., *Science*, 264:1336-1340 (1994).
Suzuki, et al., *Biochem. Biophys. Res. Commun.*, 285:991-996 (2001).
Tanzi, et al., *Science*, 235:880-884 (1987).
Tomski, et al., *Arch. Biochem. Biophys.*, 294(2): 630-638 (1992).
Vigo-Pelfrey, et al., *J. Neurochem.*, 61:1965-1968 (1993).
Whitehouse, et al., *Mol. Genet. Med.*, 3:95-137 (1993).
Yankner, et al., *Science*, 250:279-282 (1990).
Frederikse et al., "Oxidative stress increase production of β-amyloid precursor protein and β-amyloid (Aβ) in mammalian lenses, and Aβ has toxic effects on lens epithelial cells", *J. Biol. Chem.*, 271(17):10169-10174 (1996).

* cited by examiner

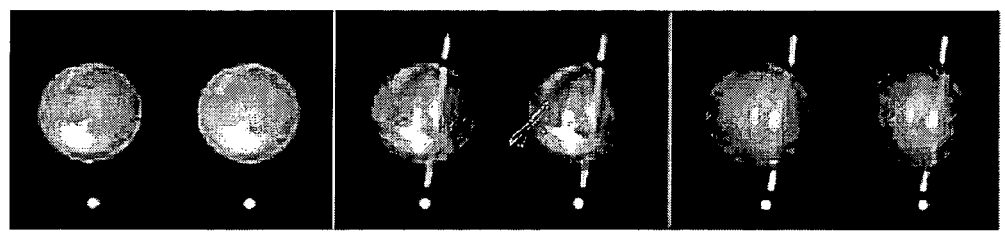
Fig. 2A
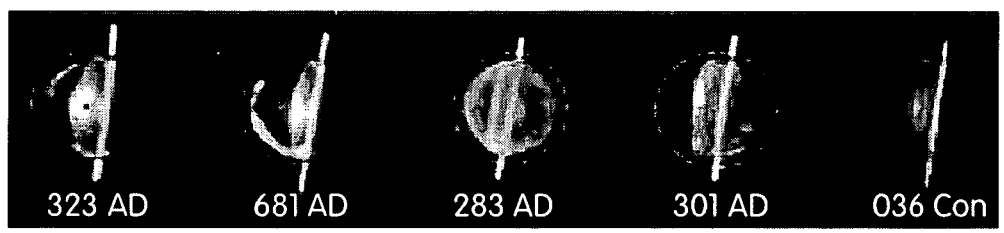
Fig. 2B
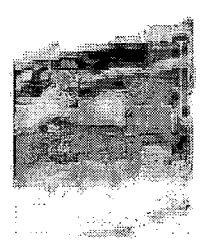  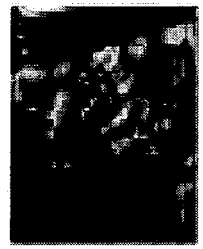
Fig. 2C  Fig. 2D  Fig. 2E
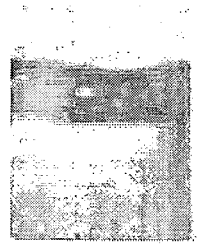  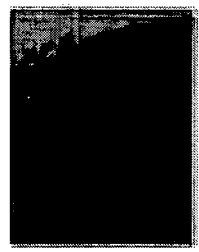
Fig. 2F  Fig. 2G  Fig. 2H
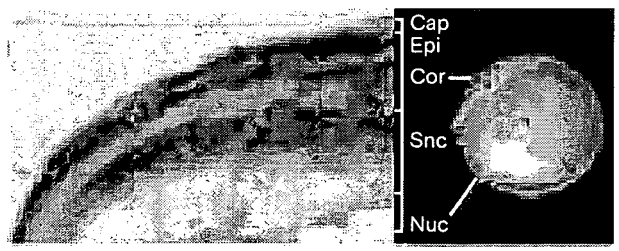
Fig. 2I

US 7,297,326 B2

OCULAR DIAGNOSIS OF ALZHEIMER'S DISEASE

This application claims priority to U.S. provisional application 60/427,153, filed Nov. 18, 2002 and to U.S. provisional application 60/452,336, filed Mar. 5, 2003; is a continuation in part of U.S. Ser. No. 10/132,779, filed on Apr. 25, 2002 now U.S. Pat. No. 6,849,249, which claims priority to U.S. provisional application 60/287,124, filed Apr. 27, 2001; and is a continuation in part of U.S. Ser. No. 09/935,126, filed on Aug. 21, 2001 now U.S. Pat. No. 7,107,092, which claims priority to U.S. provisional application 60/226,590, filed on Aug. 21, 2000; the entire contents of which are hereby incorporated by reference.

TECHNICAL FIELD

This invention relates to neurodegenerative disease.

BACKGROUND OF THE INVENTION

Alzheimer's Disease (AD) is a chronically progressive degenerative disorder of aging and is a major contributor to morbidity and modality in the elderly. AD currently accounts for about 70% of all cases of dementia and affects some 2-4 million Americans. As many as 9 million Americans may have AD by the year 2050. Epidemiological studies have estimated that if AD could be delayed by 5 years, the incidence and prevalence of AD would be cut in half. Development and execution of future therapies for AD will rely on sensitive and early diagnosis of the disease. Although much is known about the disease, there are no currently available means of early diagnosis or effective treatment.

SUMMARY OF THE INVENTION

The invention provides non-invasive methods for early and reliable detection of AD or a pre-morbid neurodegenerative state. The diagnostic methods are carried out by contacting an ocular tissue of a mammal, e.g., a human subject, with a detectably-labeled compound which binds to an amyloid protein e.g., amyloid-$\beta$ (A$\beta$). By "amyloid protein" is meant a protein or peptide that is associated with a AD neuritic senile plaque. Preferably, the amyloid protein is amyloid precursor protein (APP) or a naturally-occurring proteolytic cleavage product. APP cleavage products include A$\beta$1-40, A$\beta$2-40, A$\beta$1-42, as well as oxidized or crosslinked A$\beta$. The compounds bind to naturally-occurring variants of APP and A$\beta$, including single nucleotide polymorphic (SNP) variants. An increase in binding of the compound to an ocular tissue, e.g., an intracellular compartment of a lens cell, compared to a normal control level of binding indicates that the mammal is suffering from or is at risk of developing AD. Preferably, the compound binds to A$\beta$1-42 or another fragment of an amyloid precursor protein (APP). The compounds preferentially bind to amyloid proteins compared to other $\beta$-pleated sheet containing proteins. Preferably, the detectably-labeled compound contains a fluorescent probe. For example, the fluorescent probe or fluorophor is a Chrysamine or Chrysamine derivative compound such as {(trans, trans), -1-bromo-2,5-bis-(3-hydroxycarbonyl-4-hyrdoxy)styrlbenzene (BSB)}.

The methods are useful for in vivo drug screening to identify compounds, which inhibit A$\beta$ accumulation in the eye and brain, for pre-morbid staging AD severity, diagnosis, prognosis, and monitoring patient responses to drug therapy for AD. The degree of A$\beta$ aggregation in the cortical region of the eye is directly proportional to neuropathological A$\beta$ deposits in the brain.

An eye tissue of a test subject is contacted with the compound, allowed to penetrate cells in the lens region of the eye, and fluorescence is measured. The cortical region of the eye is evaluated by fluorescent scanning. Alternatively, the aqueous humor, i.e., the clear liquid between the cornea and the lens, of the eye is scanned. An increase of at least 10% over lens fluorescence of a normal control subject (after probe administration) indicates AD or a predisposition thereto. A normal control value typically corresponds to little or no binding of the probe to lens tissue. The level of normal lens fluorescence is the level of fluorescence detected after contacting an eye of a normal, AD-free subject (or population of subjects) with an A$\beta$-binding detectably-labeled compound. The value is optionally derived by determining the average or mean of values derived from a pool of individuals of subjects known to be free of AD (as well as free of family history or known genetic predisposition thereto). If the probe used emits light in the range of normal human lens autofluroescence (blue-green range), the level of autofluorescence is factored into the reading. For example, a 10% increase in fluorescence (after probe administration) compared to the level in the absence of the probe (autofluorescence) indicates a pathological state or predisposition to developing a neuropathological state. Preferably, baseline autofluorescence is established (prior to probe administration) for each individual.

A diagnostic level of fluorescence is preferably at least 25%, more preferably at least 50%, more preferably at least 100% greater than a normal control value. For example, detection of A$\beta$-specific probe fluorescence, which is 2-fold or more greater than a normal control value, indicates a pathological state. Since normal human lens tissue autofluoresces in the blue-green range (495 nm/520 nm), the probe preferably emits a wavelength of light outside the blue-green spectra. For example, the fluorescent probe emits a wavelength of light greater than 520 nm, e.g., fluorescence in the red, orange-red, or infrared range. Alternatively, the probe emits a wavelength less than 450 nm, e.g., in the violet or ultra-violet (UV) range.

A method for prognosis of Alzheimer's Disease includes the steps of (a) contacting ocular tissue of a mammal with a compound which binds to an amyloid polypeptide; (b) quantitating binding of the compound to ocular tissue; and (c) comparing the level of binding with a normal control level of binding. Increased levels of binding over time indicates an adverse prognosis. Test patient lens fluorescence after probe administration is compared to endogenous autofluorescence of a non-AD subject (or population of individuals) or the level of fluorescence of a non-AD subject (or population of non-AD subjects) after probe administration. The methods are also used to stage severity of disease, monitor responses to drug treatment, and screen drugs for the ability to inhibit A$\beta$ accumulation. An increased level of fluorescence (indicative of cortical lens A$\beta$ accumulation) indicates a more advanced stage of AD. A reduction in level of fluorescence (indicative of cortical lens A$\beta$ accumulation) over time indicates that a given drug inhibits A$\beta$ accumulation and indicates a positive clinical response to drug treatment.

Also within the invention are detectably-labeled A$\beta$ binding compounds which emit light outside the blue-green range. For example, the binding compounds are fluorescent probes which emit light at a wavelength between 550-700 nm. The compounds contain Texas Red or a derivative thereof.

The compounds, e.g., polypeptide ligands, organic compounds, or inorganic compounds, are isolated or purified. An "isolated" or "purified" composition is substantially free of cellular material or other contaminating proteins from the cell or tissue source from which it is derived, or substantially free from chemical precursors or other chemicals when chemically synthesized. Preferably, a preparation of a compound, e.g., a fluorescent Aβ-binding compound, is at least 75%, more preferably 80%, more preferably 85%, more preferably 90%, more preferably 95%, more preferably 98%, and most preferably 99 or 100% of the dry weight of the preparation.

"Fluorescence" is the phenomenon in which light energy ("exciting light") is absorbed by a molecule resulting in the molecule becoming "excited." After a predescribed interval such as 1 minute-24 hours, the absorbed light energy is emitted by the excited molecule. The wavelength of the emitted light is typically at a longer wavelength than the exciting light. This emitted light is referred to as fluorescent light. A molecule that exhibits fluorescence is referred to as a "fluorophor." The relationship between wavelengths of light and degree of excitation of a given fluorophor at that wavelength is described by the "excitation spectrum" of the fluorophor. The excitation spectrum is also called the excitation wavelength range. The relationship between the wavelength of light and the intensity of the fluorescence emission at that wavelength is described by the emission spectrum or fluorescence spectrum of the fluorophor. The emission spectrum is also called the emitted wavelength range. The excitation maximum is the wavelength of exciting light at which fluorescence of the fluorophor reaches maximum intensity. The emission maximum is the wavelength of light emitted by the excited fluorophor when its fluorescence is at maximum intensity.

Most fluorophors excited by and emitting visible light have an emission spectrum overlapping their excitation spectrum, although the maximum for each is different. The distance in nanometers between the excitation spectrum maximum and the emission spectrum maximum is known as the "Stokes' shift." Fluorophors with large Stokes' shifts in the visible range work best in this invention. For example, a fluorophor with an excitation maximum of 400 nm and an emission maximum of 700 nm with little or no overlap between the spectra is preferable.

The invention also provides a method of diagnosing Alzheimer's Disease in a mammal by contacting an ocular tissue with a detectably-labeled compound such as a positron emitting radionuclide. An increase in binding of the compound to the ocular tissue, as compared to the level of binding in a normal control tissue, indicates that the mammal is suffering from or is at risk for developing Alzheimer's Disease. For example, the positron emitting radionuclide is selected from the group consisting of Carbon-11, Nitrogen-13, Oxygen-15, and Fluorine-18. In some embodiments, the detectably-labeled compound is a Chrysamine compound that preferentially binds to an amyloid-β (Aβ) polypeptide, such as Aβ (1-42).

Binding is detected by imaging a cortical region of the eye or a supranuclear region of an eye. Binding may also be detected by imaging the lens (and lens subregions), the aqueous humor, the cornea, the vitreous humor, the ciliary body, the iris, and the retina. An increase in binding is a level of binding that is at least 10%; at least 25% greater; at least 50% greater; or at least 100% greater than a normal control value.

The diagnostic method is also carried out by contacting an ocular tissue of a mammal with a detectably-labeled compound such as a radioactively labeled compound. An increase in binding of the compound to the ocular tissue, as compared to the level of binding in a normal control tissue, indicates that the mammal is suffering from or is at risk for developing Alzheimer's Disease. For example, the radioactive label is $^3$H or $^{125}$I. For example, a radioactively tagged Chrysamine compound is used to determine the level of binding cortical region of the eye and/or a supranuclear region of an eye is scanned to detect and localize radioactivity. An increase of at least 10%; at least 25%; at least 50%; or at least 100% greater than a normal control value indicates AD or a predisposition thereto.

Magnetic resonance imaging is also used to determine the amount and anatomical location of an amyloid protein present in an ocular tissue. An increase in the amount of amyloid protein and a difference in the anatomical location of amyloid protein present in the ocular tissue compared to the amount of amyloid protein and the anatomical location of amyloid protein present in a normal ocular tissue indicates that the mammal is suffering from or is at risk of developing Alzheimer's Disease. For example, the amyloid protein may be an amyloid-β (Aβ) polypeptide such as Aβ (1-40), Aβ (2-40), or Aβ (1-42). Detection by MRI of Aβ in a cortical region of the eye or on a supranuclear region of an eye indicates AD or a risk of developing the disease.

The methods described above are also useful for prognosis of Alzheimer's Disease. For example, a prognostic method involves the steps of contacting ocular tissue of a mammal with a compound which binds to an amyloid polypeptide; quantitating the level of association of the compound with said ocular tissue; and comparing the level of association with a normal control level of association. Increasing levels of association over time indicates an adverse prognosis. In these methods, the quantitating step may be accomplished by, e.g., positron emission tomography, radioimaging, radioimmunoassay, or magnetic resonance imaging. Other imaging techniques include interferometry and polarimetry. The methods described herein offer several advantages over existing approaches to AD diagnosis. First, the method is carried out ante-mortem and accurately and reliably identifies Aβ accumulation in living tissues. Prior to the invention, reliable detection of deposits was made from studying autopsy samples of the brains of AD patients. Second, the method is non-invasive; no biopsy of tissue is required. The method utilizes physiologically-compatible probes. Moreover, the scanning procedure itself takes a matter of seconds, e.g., 30 seconds-minutes. Finally, the specificity and sensitivity of detection is high because of the unique anatomical pattern of Aβ accumulation, i.e., the cortical region of the lens in a non-diseased state is characterized by little or no protein accumulation/aggregation. Even small amounts of Aβ protein accumulation is stable and easily detectable in this region of the eye.

Other features, objects, and advantages of the invention will be apparent from the description and drawings.

BRIEF DESCRIPTION OF THE DRAWINGS

FIG. 1 shows the identification and characterization of β-APP and Aβ in the adult human lens.

FIG. 2 is a series of photographs showing the gross pathology and histology of postmortem human lenses from representative donors with and without AD neuropathology. FIG. 2A is a series of stereoscopic photomicrographs without (left-hand panel) and with (middle panel) slitlamp illumination of a single lens from an 80 y.o. female with severe AD. Visual convergence of white dots beneath the images indicates stereoscopy. Supranuclear cataracts are apparent in the superior and inferior left-hand quandrants. Control lens (right-hand panel) from an 80 y.o. female without AD does not exhibit supranuclear cataracts. FIG. 2B shows a series of donor lenses. Donor lens #323 (80 y.o. female, AD): supranuclear cataract are shown with a white dashed arc and nuclear cataract is shown with a series of asterisks and nuclear brunescence are co-morbidly present. Donor lens #681 (68 y.o. female, AD): supranuclear cataract is shown with a dashed white arc. Donor lens #283 (82 y.o. female, AD): supranuclear cataract is shown with a dashed white arc. Axial posterior subcapsular cataract is co-morbidly present. Donor lens #301 (75 y.o. female, AD): patchy circumferential supranuclear cataract is shown with a dashed white arc. Small areas of cortical opacification are also present. Donor lens #086 (63 y.o. female, frontotemporal dementia and Parkinson's disease) without evidence of supranuclear or cortical cataracts. FIG. 2C shows that anti-Aβ immunostaining is evident in the cortical and supranuclear regions of this lens from 80 y.o. female with neuropathologically confirmed AD. FIG. 2D shows Congo Red staining in same AD lens as in FIG. 2C. FIG. 2E shows apple-green birefringence in AD lens cortex and supranuclear regions in same AD lens as in FIG. 2D. FIG. 2F shows faint Anti-Aβ immunostaining in this control lens from an 80 y.o. female without AD. FIG. 2G shows Congo Red staining in same control lens as in FIG. 2F. FIG. 2H shows faint birefringence in same control lens section as in FIG. 2G. FIG. 2I shows the correlation of histological localization of Aβ and cataract pathology in AD lens. FIG. 2J is an anti-Aβ IEM photomicrograph of the deep cortical region of lens from an 82 y.o. female AD donor. Numerous anti-Aβ-immunoreactive clusters are present (black arrows) within the lens fiber cells. Aβ-immunogold staining was not detected in extracellular regions. Scale bar=200 nm. FIG. 2K is a higher magnification of same AD lens section as in FIG. 2J demonstrating the increased electron-density of the cytosolic Aβ-immunoreactive aggregates (black arrows). FIG. 2L is an anti-Aβ IEM photomicrograph of the deep cortical region of control lens from a 76 y.o. female without AD. Scattered anti-Aβ-immunoreactive clusters were evident in the cytoplasm of some lens fiber cells. Scale bar=200 nm. FIG. 2M and FIG. 2N are control sections demonstrating the absence of immunostaining in the lens specimen from the same AD donor as in FIGS. 2J and 2K probed with anti-AβmAb 4G8 pre-absorbed with synthetic human Aβ (FIG. 2M) or anti-β-APP mAb 22C 11 (FIG. 2N). [Scale bars=200 nm]. FIG. 2O is an AD lens demonstrating double immunogold staining for Aβ and αB-crystallin within a single electron-dense cytosolic aggregate. Larger gold particles (15 nm diameter) detect Aβ immunoreactivity, whereas smaller gold particles (10 nm diameter) detect α-crystallin immunoreactivity. As used throughout FIG. 2, Cap=capsule; epi=epithelium; cor=cortex; snc=supranucleaus; and nuc=nucleus.

FIG. 3 shows various Aβ and human lens protein interactions.

DETAILED DESCRIPTION

The non-invasive ocular diagnostic methods described herein facilitate diagnosing, prognosing, and monitoring AD and related neurodegenerative disorders, which are mediated by accumulation of amyloid proteins. The disease process involves pathogenic accumulation of Aβ peptides in vulnerable regions of the brain. The invention is based on the discovery that these same Aβ peptides accumulate as microaggregates in ocular cells and, in particular, within the cortical region of the lens in AD patients.

Figure 5A:
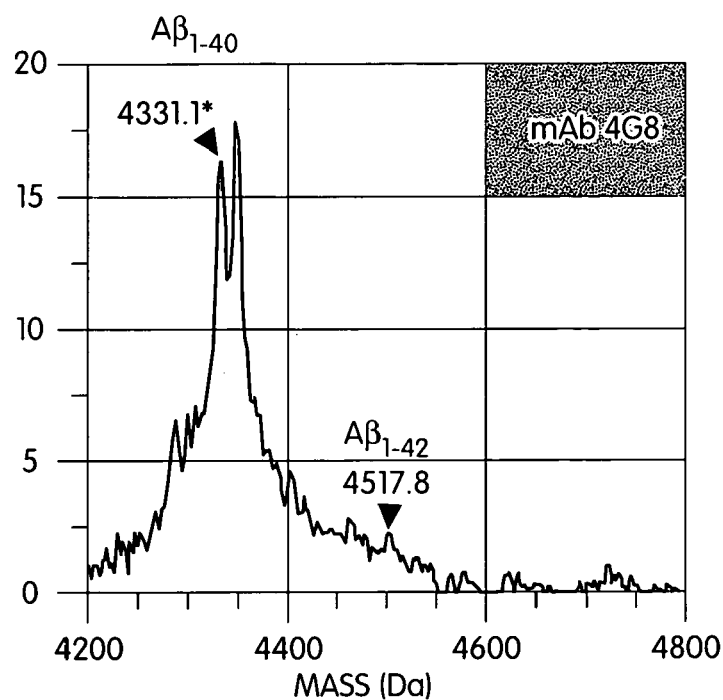
FIGS. 5A-B are line graphs showing a detection and biochemical conformation of Aβ in human aqueous humor from living patients. Aqueous humor was obtained by needle aspiration and analyzed by Surface Enhanced Laser Dissorption Ionization (SELDI) Mass Spectroscopy. An Aβ-specific monoclonal antibody immobilized on a microchip array is contacted with a patient-derived sample, exposed to a laser, and subjected to mass spectroscopy analysis. Non-immune immunoglobulin served as the negative control (FIG. 5B). Primary aqueous humor was found to contain approximately 20 micrograms/leter of Aβ. $A\beta_{40}$ and oxidized Aβ $(Aβ_{40})_{ox}$. $Aβ_{40}$ was present in greater amounts than $Aβ_{42}$. The Aβ detected was found to be in an oxidized form (oxidized methionine residue).
Figure 5B:
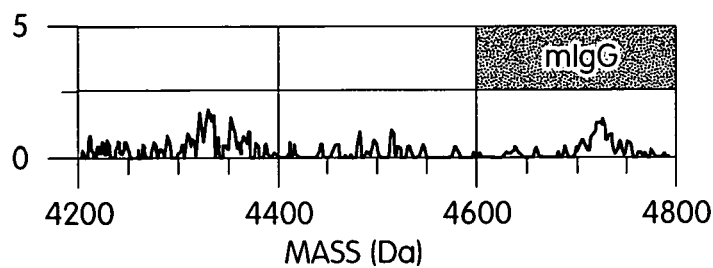
Figure 6:
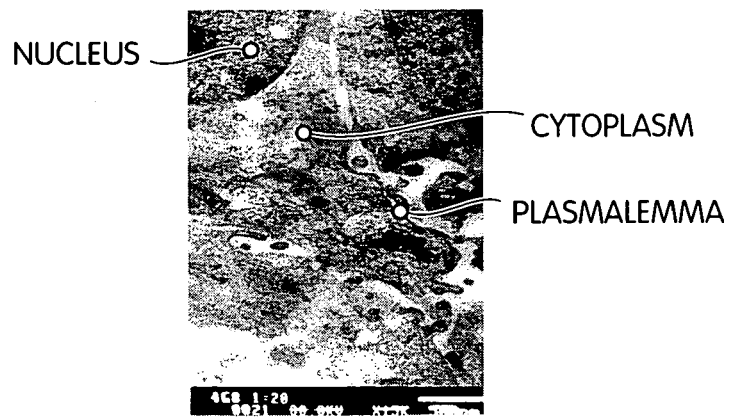
FIG. 6 is photomicrograph of lens epithelial cells. A monolayer of lens epithelial cells is located on the anterior surface of the lens. Epithelial cells were found to secrete Aβ, rather than retain it in the cytosol. These data indicate that lens epithelial cells are a source of Aβ in the eye.

In addition to accumulation in the cortex of the eye, Aβ accumulates in the aqueous humor of the eye, e.g., in the anterior chamber. (See FIGS. 5A-B and 6). Primary aqueous humor from living patients was examined. The results demonstrate that Aβ is present in both the human lens and the aqueous humor. See FIGS. 5A-B. Aβ is present as cytoplasmic, nonfibrillar amyloid in fiber cells and is secreted by lens epithelial cells. (See FIG. 6). Moreover, Aβ complexes with cytosolic lens proteins, including $α_b$-crystallin. Aβ also induces aggregation via metalloprotein redox reactions.

Progression of the disease leads to cell death and accumulation of extracellular Aβ peptides. Protein aggregation may progress to the development of a relatively rare cataract ("supranuclear", or deep cortical, cataract). Such supranuclear cataracts were detected in a transgenic mouse model of AD and in post-mortem lenses from human patients neuropathologically confirmed for AD. The diagnostic methods of the invention are tools by which to monitor Aβ aggregation and accumulation in the lens as a biomarker for similar events occurring in considerably less accessible cerebral compartments. Pertinent ocular structures in which protein aggregation and accumulation can be measured include the lens (and lens subregions), of the aqueous humor, the cornea, the vitreous humor, the ciliary body, the iris, and the retina.

The presence of or an increase in the amount of aggregate in the supranuclear and/or cortical lens regions of the test mammal compared to a normal control value indicates that the test mammal is suffering from, or is at risk of, developing an amyloidogenic disorder. A normal control value corresponds to a value derived from testing an age-matched individual known to not have an amyloidogenic disorder or a value derived from a pool of normal, healthy (non-AD) individuals. An amyloidogenic disorder is one that is characterized by deposition or accumulation of an amyloid protein or fragment thereof in the brain of an individual. Amyloidogenic disorders include AD, Familial AD, Sporadic AD, Creutzfeld-Jakob disease, variant Creutzfeld-Jakob disease, spongiform encephalopathies, Prion diseases (including scrapie, bovine spongiform encephalopathy, and other veterinary prionopathies), Parkinson's disease, Huntington's disease (and trinucleotide repeat diseases), amyotrophic lateral sclerosis, Down's Syndrome (Trisomy 21), Pick's Disease (Frontotemporal Dementia), Lewy Body Disease, neurodegenration with brain iron accumulation (Hallervorden-Spatz Disease), synucleinopathies (including Parkinson's disease, multiple system atrophy, dementia with Lewy Bodies, and others), neuronal intranuclear inclusion disease, tauopathies (including progressive supranuclear palsy, Pick's disease, corticobasal degeneration, hereditary frontotemporal dementia (with or without Parkinsonism), and Guam amyotrophic lateral sclerosis/parkinsonism dementia complex). These disorders may occur alone or in various combinations. For example, individuals with AD are characterized by extensive accumulation of amyloid in the brain in the form of senile plaques, which contain a core of amyloid fibrils surrounded by dystrophic neurites. Some of these patients exhibit clinical signs and symptoms, as well as neuropathological hallmarks, of Lewy Body disease.

Chrysamine G and derivatives thereof are known in the art (e.g., U.S. Pat. Nos. 6,133,259; 6,168,776; 6,114,175). These compounds bind to Aβ peptides, but are not fluorescent. The diagnostic methods utilize a highly lipophilic fluorescent amyloid-binding Chrysamine G derivative to detect Aβ peptides in the eye. After contacting ocular tissue with an Aβ-specific probe, non-invasive scanning using standard ocular fluorphotometric techniques reveals the degree of binding. Ocular fluorimeters and other eye imaging devices are known in the art (e.g., U.S. Pat. Nos. 6,198,532 and 6,013,034).

The methods take advantage of bioavailable lipophilic fluorescent probes. Such fluorophors and probes are commercially-available, e.g., from Molecular Probes, Inc. Eugene, Oreg. Some dyes, e.g., X-34 or {(trans, trans), -1-bromo-2,5-bis-(3-hydroxycarbonyl-4-hyrdoxy)styrlbenzene (BSB)} (Styren et al., 2000, J. Histochem. 48:1223-1232; Link et al., 2001, Neurobiol. Aging 22:217-226; and Skrovonsky et al., 2000, Proc. Natl., Acad. Sci. U.S.A. 97:7609-7614) have been used to analyze brain tissue (but not eye tissue). These probes emit light in the blue-green range, thus the level of fluorescence, which is diagnostically relevant, exceeds the amount of human lens autofluorescence in the blue-green range.

The methods of the invention may also employ radioactively labeled probes that are detected using methods such as radioligand binding, radioimmunoassay, and radioimaging. Such probes may be radioactively labeled using a radioisotope such as $^3H$, $^{14}C$, $^{22}Na$, $^{32}P$, $^{35}S$, $^{42}K$, $^{45}Ca$, $^{59}Fe$, $^{125}I$, or $^{203}Hg$. Alternatively, the amount of amyloid protein present in ocular tissue is determined by positron emission tomography (PET) and magnetic resonance imaging.

The probes utilized in the diagnostic methods specifically bind to Aβ and (Aβ-associated proteins relative to other β-pleated sheet-containing proteins or polypeptides. The probes are applied to the eye in a liquid or ointment form. The lipophilicity of the compounds facilitates penetration the intervening structures. The compounds bind with high avidity to accumulations of Aβ within the lens and other ocular structures. For example, the compounds are formulated in a solution with an excipient, e.g., DMSO, to improve tissue and cellular penetration of the fluorescent Aβ-binding compound. After contacting the eye with the compound, the compound is allowed to penetrate ocular tissues for a period of time, e.g., 1 minute to 5 hour, prior to fluorescent scanning, PET scanning, autoradiographic scanning, radioimaging, radioimmunoassay, or magnetic resonance imaging of the eye. Preferably, the eye is contacted with the compound for at least one hour prior to scanning or imaging. The eye may be contacted with the probe for up to a day or more prior to scanning. Ratiometric and other analyses of fluorophotometric or radioactive or positron emitting signals before and after ocular application and distribution of the probes within specific subregions of the ocular structures quantitatively reveal the degree and localization of Aβ accumulations associated with the AD disease state. An increase in the amount of accumulated Aβ peptides compared to a normal control value indicates a neurodegenerative condition such as AD.

The region of the lens in which an AD-associated supranuclear cataract forms is not predisposed to form high molecular weight aggregates compared to the nuclear region of the lens. In addition, lens proteins, once formed, are uniquely stable for long periods of time. Thus, proteins and peptides in the lens are not readily cleared and tend to accumulate, whereas in the brain multiple mechanisms are involved in the clearance of deleterious Aβ peptides. Thus, the unique situation of lens Aβ promotes early accumulation relative to the brain. This property of the lens increases the accuracy and reliability of detecting Aβ-mediated aggregation and accumulation very early in the course of the disease (e.g., prior to the appearance of overt cognitive or neurological symptoms).

Amyloid Proteins

AD is characterized by severe oxidative damage and pathologic accumulation of insoluble protein in vulnerable brain regions. The toxic amyloid Aβ peptides are generally considered to be major pathogenic participants in AD. These various peptides are generated by cleavage of a larger protein called the β-amyloid precursor protein (APP) (Selkoe et al., 2000, Annal. of N.Y. Acad. Sci. 924:17-25). Proteins called presenilins (PS1, PS2) may mediate cleavage. Other neuritic plaque-associated proteins include β-amyloid secretase enzymes I and II (BASE I and II) which associate with amyloid proteins. Some of the resulting Aβ peptides are more toxic than others. Elevation of specific Aβ peptides in the brain is believed to be causally associated with all known forms of AD. This generally accepted "Aβ hypothesis" states that Aβ generation, deposition and/or accumulation in the brain is an important final common pathway which underlies the disease process in this devastating neurological disorder.

Amyloid proteins (Aβ, APP, PS1, PS2) are also expressed in the lens of the mammalian eye. Aβ aggregation occurs both inside and outside cells, depending upon the state of progression of the neurodegenerative disease. Aβ is capable of aberrantly interacting with proteins in the lens, such as the long-lived α-crystallins. The diagnostic methods described herein are based on the following observations: i) Aβ peptides accumulate in specific subregions of the lens, ii) Aβ peptides potently promote lens protein aggregation, and iii) a distinctive deep supranuclear zonular cataract is associated with Aβ overexpression in a well-characterized animal model of AD, the amyloid-bearing APP-mutant Tg2576 transgenic mouse, and in post-mortem lenses derived from human patients having been diagnosed independently and neuropathologically with AD.

Detection of AD-associated Protein Accumulation in the Eye

The data described herein indicate that in vivo examination of lens proteins yield diagnostically-relevant information about Aβ accumulation, which cannot be obtained from less accessible organs such as the brain. A significant advantage of the methods of the invention is that they are non-invasive. The non-invasive methods are useful in in vivo drug screening, diagnosing, prognosing, and monitoring responses of AD patients to therapeutic intervention.

Aβ-specific probes are lipophilic and relatively uncharged for PET, MRI, other non-fluorescent techniques. The lipophilic nature of the probes mediates efficient access to eye tissues and across the lipophilic barrier of the eye and cell membranes of eye structures. In addition, lipophilicity facilitates access to the intracellular compartments of cells in the lens region of the eye. This aspect of the probes is critical for early disease detection, because in the early stages of AD, Aβ accumulates inside the cells rather than extracellularly. Only as the disease progresses and cells die, do extracellular accumulations or plaques become evident.

Fluorescent Detection

The technique takes advantage of a lipophilic fluorescent high affinity Aβ-binding probe such as {(trans, trans), -1-bromo-2,5-bis-(3-hydroxycarbonyl-4-hydroxy)styrlbenzene (BSB)}. This compound (as well as lipophilic fluorescent Aβ-binding derivatives) is applied to the eye and allowed to distribute into the lens.

Amyloidophilic dyes bind to amyloid fibrils. Suitable dyes include crystal violet, methyl violet, losin, brilliant cresol violet and direct red. Preferred dyes include thioflavins, particularly thioflavin T, thioflavin S, and Congo Red. See U.S. Pat. No. 6,423,270 incorporated herein by reference. The other amyloidophilic probes bind to β-pleated sheet protein structures present in the eye, whereas the Chrysamine-based probes specifically bind to Aβ and other fragments of APP. Chrysamine G and other amyloid-binding derivative of Congo Red are useful as the amyloid binding moiety of the probe; a detectable label, e.g., a fluorophor is attached to allow fluorescent scanning. Chrysamine and other Congo Red derivatives bind to amyloid proteins through a bedentate attachment spanning several amyloid peptide chains.

If more than one dye is added to a sample, the order of addition may be important. It has been found, for example, that thioflavin T should be used before Congo red because the addition of Congo red before thioflavin T results in quencing of the thioflavin T fluorescence.

Fluoroescence assays are conducted according to a standard protocols. To determine whether the Aβ-induced aggregation of hTSLP was accompanied by conformational changes, the total β-sheet content of the protein mixture was measured by monitoring thioflavin-T fluorescence. Solutions of hTSLP incubated with $hA\beta_{1-42}$ exhibited markedly increased thioflavin-T fluorescence compared to hTSLP alone, indicating that Aβ-potentiated hTSLP aggregation is associated with enhanced β-sheet content.

The amount of Aβ-binding along the optical axis is monitored by scanning fluorophotometric techniques. Fluorescence along the optical axis is measured prior to application of the probe to determine baseline autofluorescence. Fluorescence is then measured again after application of the probe. Fluorescence is measured in the supranuclear deep cortical region of the anterior and posterior lens as well as in the nuclear region. Fluorescence may also be measured in the lens (and lens subregions), the aqueous humor, the cornea, the vitreous humor, the ciliary body, the iris, and the retina. The ratio of cortical fluorescence to nuclear fluorescence before application of the probe is compared to the ratio after probe application. For example, the ratio of cortical to nuclear fluorescence before probe application is 2:2; after probe application, the ratio is 10:2. The comparison indicates Aβ accumulation (and a diagnosis of AD or a predisposition to developing AD). A normal control value includes minimal or no detectable fluorescence in the cortical region after probe administration. Binding of a lipophilic fluorescent Aβ-binding probe, as indicated by an increased fluorescent signal in the cortical lens region compared to the nuclear region, yields a metric which is correlated with disease presence or absence. The degree of Aβ accumulation is greater and more rapid within the lens compared to other tissues. This accumulation is indicative of the stage of the disease, i.e., greater accumulation is directly correlated with a more advanced stage of AD or a related neurodegenerative state. The magnitude of fluorescence above baseline autofluorescence correlates with disease severity. These binding data serve as a biological indicator or biomarker of Aβ deposition within the brain.

In addition to the probes described above which emit light in the blue-green region of the light spectrum, the methods also utilize other probes, which emit a fluorescent signal outside (longer or shorter) the range of normal lens autofluorescence (495 nm/520 nm). Various small molecular fluorophors are conjugated to amyloid binding compounds, e.g., Chrysamine G or clioquinol, using methods known in the art. For example, long wave fluorophors, e.g., Texas Red and derivatives thereof, are used. Such dyes allow scanning at wavelengths, e.g., in the far infrared range, without interference of normal lens autofluorescence.

Both synthetic and physiological amyloid samples display a linear relationship between side scatter and forward scatter, which is believed to be indicative of the structure of the amyloid fibrils, i.e., linear aggregates composed of identical, repeating sub-units. Labeling the preparations with Congo red and/or thioflavin T results in a large fluorescent signal using propidium iodide and fluoresce in isothiocyanate filters, The amount of thioflavin T fluorescence is proportional to the amount of dye bound to an individual amyloid fibril, which in turn is positively correlated with its length. (U.S. Pat. No. 6,423,270).

Positron Emission Tomography (PET)

Positron Emission Tomography (PET) is a technique for measuring the concentrations and movement of positron-emitting radioisotopes within the tissues of living subjects. First, a selected compound, such as a probe that binds to for Aβ and other fragments of APP is labeled with a positron-emitting radionuclide. This labeled component is then administered to the subject's eye. The distribution of the positron activity as a function of time is then imaged as a function of time by means of emission tomography.

Improved anatomic localization of activity obtained by overlaying or imprinting the information obtained from PET onto more detailed images obtained from magnetic resonance imaging (MRIs) or CT-scans.

A wide range of compounds can be used in PET. Typically, suitable positron-emitting radionuclides have short half-lives and high radiation energies, when compared with radioisotopes generally used in biomedical research. Examples of positron-emitting radionuclides used in PET include: Carbon-11, Nitrogen-13, Oxygen-15, and Fluorine-18, which have half-lives of 20 minutes, 10 minutes, 2 minutes, and 110 minutes, respectively. These radioactive forms of the natural elements that emit radiation that will pass through the body for external detection. Natural substrates, substrate analogs, and drugs are labeled with these radioisotopes without altering their chemical and/or biological properties. An advantage of this method of detection is that the short half-lives of these radionuclide tracers allow large doses to be administered to patients with low radiation exposure, which, in turn, enables studies to be repeatedly performed.

PET imaging is indirect and relies on computerized reconstruction procedures to produce tomographic images. PET imaging uses tomography to detect positron-emission. Radionuclide decay reduces excess positive charges on the nucleus in two ways: (1) neutralization of a positive charge with the negative charge of an electron or (2) the emission of a positron from the nucleus. The positron then combines with an electron from the surrounding environment and annihilates. Upon annihilation, both the positron and the electron are then converted to electromagnetic radiation, in the form of two high-energy (511-keV) gamma rays (photons), which are emitted 180 degrees away from each other. The resulting radiation can be detected externally using crystal scintillation detectors and is used to measure the quantity and the location of the positron-emitting source. Simultaneous detection of these two photons by detection means placed on opposite sides of an object (e.g. the patient's eyes or the patient's head) establishes the site of positron annihilation on or about a line connecting the centers of the two detection means. The crystal scintillation detectors detect the emitted photons and tomographically reconstruct the point of origin of the positron-electron collision. Burggren et al., Curr Topics in Med. Chem. 2:385-93 (2002), incorporated herein by reference.

Simultaneous detection provides a precise field of view having uniform sensitivities. PET is useful to detect supranuclear cataracts formed by Aβ accumulation in the eye.

Magnetic Resonance Imaging

Magnetic resonance imaging (MRI) is an imaging technique used in medical settings to produce high quality images of the inside of the human body. Structural MRI provides a tool useful for observing structural differences in a non-invasive manner. Burggren et al., Curr Topics in Med. Chem. 2:385-93 (2002), incorporated herein by reference. After placing a subject into a strong magnetic field, the application of a brief radio frequency electromagnetic pulse disturbs the equilibrium of the proton nuclei within a subject and introduces a magnetization that can be detected as a radio signal and formed into an image.

MRI uses radio waves and a strong magnetic field rather than x-rays to provide clear and detailed pictures of internal organs and tissues such as brain and ocular tissues. The technique is used to evaluate some body structures e.g. supranuclear eye tissue that may be difficult to image visible with other imaging methods. For example, MRI can be used to produce a high resolution image of the brain's internal structure.

After placing a subject into the strong magnetic field, the application of a brief radio frequency electromagnetic pulse disturbs the equilibrium of the proton nuclei within a subject and introduces a magnetization that can be detected as a radio signal and formed into an image. Because the rate at which a magnetic resonance (MR) signal decays in these protons depends on intrinsic factors, signals decay at different rates in different tissue types. Thus, the resulting image contains different signal intensities in various regions of the body depending on the decay rate to the protons that make up that area.

An MRI scanner contains a large magnet that induces different chemical elements to emit distinctive radio signals. This signal data is then translated into 2-D pictures of the brain, slice by slice, and the resulting 2-D pictures can be combined to create 3-D views.

MRI equipment includes a horizontal tube (the bore of the magnet) running through the magnet from front to back. The magnetic force exerted on an object increases exponentially as it nears the magnet. The MRI machinery applies a radio frequency (RF) pulse that is specific only to hydrogen. The system directs the pulse toward the area of the body being examined. This pulse then causes the protons in the area under examination to absorb the energy required to make them spin ("precess") in a different direction, which is known as the "resonance" part of MRI. The RF pulse forces the one or two extra, unmatched protons per million to spin at a particular frequency and in a particular direction. This frequency is known as the Larmour frequency, which can be calculated, based on the particular tissue being imaged and the strength of the main magnetic field of the MRI equipment.

Typically, RF pulses are applied through coils that conform to the part of the body being examined and that are located within the MRI machinery. Almost simultaneously, the three gradient magnets are activated, which are arranged in such a manner inside the main magnet that when they are turned on and off very rapidly in a specific manner, they alter the main magnetic field on a very local level.

When the RF pulse is turned off, the hydrogen protons begin to slowly return to their natural alignment within the magnetic field and release their excess stored energy, thereby giving off a signal that is picked up by the coil and sent to the computer system. This mathematical data is converted, through the use of a Fourier transform, into a picture that can be put on film. This step represents the "imaging" part of MRI. Imaging modalities such as MRI use injectable contrasts, or dyes, for certain procedures. MRI contrast works by altering the local magnetic field in the tissue to be examined. Normal and abnormal tissue will respond differently to this slight alteration, which yields differing signals that are transferred to the images, allowing us to visualize many different types of tissue abnormalities and disease processes.

Functional Magnetic Resonance Imaging (fMRI)

fMRI is a technique that has several advantages over PET, such as noninvasiveness, increased spatial and temporal resolution, and repeatability because fMRI does not involve exposure to radiation. For example, fMRI monitors blood flow, which is a marker for neural activity, during an active state to assess which regions are involved in the completion of the task. When used to detect Alzheimer's Disease, a "cognitive stress test" can be used to identify subtle abnormalities that would normally go undetected in a resting state. fMRI and PET are used in conjunction to improve the early detection of cognitive changes related to AD.

When particular neural regions become more active, a corresponding change in glucose and oxygen utilization is observed. As oxygenated and deoxygenated hemoglobin have slightly different magnetization properties fMRI defects changes in blood supply when brain regions are activated during a particular task. Pauling et al., Proc. Natl. Acad. Sci USA 22:210-216 (1936). MR signals, which are induced by an RF pulse, decay more rapidly for deoxyhemoglobin than for oxyhemoglobin, and this contrast ("blood oxygenation level-dependent (BOLD) contrast") is visualized and formed into an image. Ogawa et al., Proc. Natl. Acad. Sci USA 87:9868-72 (1990). The increase in oxygenated blood levels following neural activity appears to greater than what is actually used by an active region. Fox et al., Proc. Natl. Acad. Sci USA 83:1140-44 (1986). Therefore, a comparison of the excess of oxygenated blood on the venous side compared to the resting state can be used to determine which neural regions are active during a particular task. Burggren et al., Curr Topics in Med. Chem. 2:385-93 (2002), incorporated herein by reference Detection of Radiolabeleld Aβ Probes Radioimmunoassays (RIAs) include any method for detecting or quantitating antigens or antibodies utilizing radiolabeled reactants. RIAs are used to detect very small quantities of antigens or antibodies, even in complex mixtures such as those encountered in bodily tissues Radioligand Binding A radioligand is a radioactively labeled ligand probe used to locate target composition, e.g., Aβ. For example, a compound that binds to Aβ is tagged with a radioactive label. Ligands are radioactively labeled using $^3$H or $^{125}$I, another clinically acceptable radiolabel known in the art. Following contacting a target tissue (e.g. ocular tissue or neural tissue) with the labeled Aβ-binding composition, the target tissue is imaged or scanned to detect accumulation in a bodily tissue. Accumulation of label in a supranuclear region of the eye indicates a pathological state Scanning Laser Polarimetry (SLP)

Scanning laser polarimetry (SLP) can be used to obtain a quantitative measurement of an eye structure, such as the retinal nerve fiber layer, that cannot be easily assessed by other methods. SLP is able to measure the retinal nerve fiber layer directly and is very sensitive to detecting change, often prior to the onset of significant cellular loss. In fact, in some patients, changes in the retinal nerve fiber layer (i.e., damage to 30-50% of the nerve fibers) have been shown to occur up to 6 years before there is a detectable field of vision loss using standard visual field testing techniques.

In SLP, a near infrared wavelength laser double enter the eye at a specific orientation, passes through the tubules of the retinal nerve fiber layer, and is split into two parallel rays due to birefringence, which an optical property of the retinal nerve fiber layer. Birefringence is a property of the tissue that causes a change in the polarization of light which passes through it. There are two components to birefringence: orientation (or axis) and magnitude. Once the laser passes through the retinal nerve fiber layer, the two rays travel at different speeds, and the difference in speeds, which is know as the retardation, is directly correlated to the layer thickness of the retinal nerve fibers.

Fluorescence Correlation Spectroscopy (FCS)

Fluorescence correlation spectroscopy (FCS) is a technique where spontaneous fluorescence intensity fluctuations are measured in a microscopic detection volume of approximately 1 femtoliter defined by a tightly focused laser beam. Intensity fluctuations measured by FCS represent changes in either the number or the fluorescence quantum yield of molecules present in the detection volume. Typically, small, rapidly diffusing molecules (i.e. free fluorescent ligands) produce rapidly fluctuating intensity patterns and are detected as a series of short, randomized fluorescence bursts, whereas larger molecules (i.e. macromolecule-bound ligands) are less mobile and produce more slowly fluctuating (i.e. more highly autocorrelated) sustained bursts of time-dependent fluorescence.

FCS is used to monitor many different biomolecular association and dissociation processes such as Aβ aggregation in eye tissues. Laser sources for the excitation in FCS include the 488 nm argon-ion spectral line, the 543 nm and 633 nm He—Ne laser spectral lines and the 568 nm and 647 nm Ar—Kr laser spectral lines.

Additionally, FCS allows the measurement of the translational diffusion coefficient of macromolecules, the counting of the number of fluorescent molecules under observation, and the relative fluorescence yield of different molecules in a non-homogeneous solution, thereby permitting the amount of each species to be discriminated. The technique is based on the measurement of fluctuations of the fluorescence, which can be due to the diffusion of the fluorophore in the excitation volume or to a change of fluorescence quantum yield due to chemical reactions.

Two-photon excitation (TPE) has also recently been applied to FCS because of the inherent spatial confinement of excitation, diminished photobleaching and phototoxicity, less scattering and better optical penetration in turbid media. Dual-color cross-correlation FCS can be used to measure the cross-correlation of the time-dependent fluroscence intensities of two spectrally distinct dyes, instead of the conventional autocorrelation for a single dye. This modification of the technique results in cross-correlated quantitation of interacting molecules being generated by molecules or complexes labeled with both dyes, thereby allowing quantitation of interacting molecules without reference to their diffusion characteristics. In additional, FCS measurements can also be obtained using TPE in combination with dual-color cross-correlation.

The invention will be further described in the following examples, which do not limit the scope of the invention described in the claims.

EXAMPLE 1

AD-associated Cataract Formation

Advanced Aβ accumulation in eye tissues leads to cataract formation. Unlike the brain, the region of the lens of the eye to be scanned is characterized by low protein turnover. Proteins in the lens are stable and not cleared for decades. Thus, increased production of APP proteins, e.g., Aβ peptides, are detected very early in the progression of the disease and remain stable and detectable for long periods of time.

AD is characterized by cerebral accumulation of protein aggregates composed of Aβ peptides. Prior to or concurrently with accumulation of Aβ peptides in the brain, the peptides accumulate and are detectable n eye tissues. AD-associated deep cortical (supranuclear) cataract formation has now been detected in lenses from postmortem human AD patients and amyloid-bearing Tg2576 transgenic mice.

Aβ peptides in the lens were analyzed using slit lamp photomicroscoscopy, Aβ-Immunogold electron microscopy (EM), quantitative Western blot, co-immunoprecipitation, and in vitro turbidometry. Lenses from neuropathologically-confirmed AD cases show cataracts within the supranuclear lens region. In normal control subjects, cataract formation in this region is rare. Aβ accumulation and supranuclear cataracts were detected in post-mortem lens tissue of AD patients and in Tg2576 transgenic mice, an art-recognized model for human AD. EM studies of human AD lenses showed clusters of Aβ-immunoreactive microaggregates within the cortical fiber cell cytoplasm. Most lens Aβ is associated with other proteins, including Aβ-crystallin. Aβ potently promotes human lens protein aggregation through trace metal-dependent oxidative mechanisms.

These data indicate that intracellular Aβ protein aggregation leads to supranuclear cataract formation. Accumulation of Aβ-associated lens aggregates occurs early in AD and remain in situ. Thus, the lens provides a peripherally accessible "molecular window" on cerebral amyloidogenic processes. The non-invasive diagnostic and monitoring approaches for quantitating Aβ in the eye allow early and reliable identification of AD, patients with sub-clinical AD or who are predisposed to developing a neurodegenerative condition such as AD.

EXAMPLE 2

Amyloidogenic, Cytotoxic, and Redox Profiles of the Aβ Peptides

Age-related cataracts (ARC) and Alzheimer's disease (AD) are characterized by oxidative damage and pathologic accumulation of aggregated protein. Aβ peptides and AD-associated proteins are expressed in lens. Metalloprotein reactions correlate with amyloidogenic, cytotoxic, and redox profiles of the different Aβ peptides.

The contribution of Aβ peptides and metalloprotein chemistry to lens protein aggregation was studied as follows. Lenses from amyloid-bearing Tg+ transgenic (vs Tg−) mice and human specimens were examined by slitlamp photomicroscopy and analyzed for Aβ and APP by quantitative Western blot, EM, and immunohistochemistry. In vitro aggregation studies were carried out by incubating soluble total lens protein (TLP) with synthetic Aβ peptides, chelators, antioxidant scavengers, followed by optical density analysis, Western blot, and standard amyloid assays.

The data indicated that 1) Aβ and APP are expressed in lens; 2) Aβ is found as monomeric, oligomeric, crosslinked, and aggregated species; 3) Tg2576 APP-mutant transgenic mice develop bilateral supranuclear "zonular" cataracts; 4) in vitro TLP aggregation depends on trace metal and reactive oxygen specks (ROS); and 5) Aβ, especially the highly amyloidogenic human Aβ1-42, markedly potentiates TLP aggregation in a metal/ROS-dependent and peptide specific manner. Aβ1-42 in lenses contributes to cataractogenesis and is indicative of AD or a predisposition thereto. The data also suggest that processes which contribute to the development of AD and ARC are biochemically linked.

Metals such as copper, zinc, and iron become strongly associated with Aβ. The metals colocalize with Aβ accumulations or plaques. Accordingly, a lipophilic fluorescent metal chelating agent, e.g., clioquinol, is useful to detect Aβ deposits in the cortical region of the lens. Metal binding compounds are used alone (provided they exhibit detectable fluorescence) or are modified by attachment of a fluorophor to confer or augment fluorescence. In other embodiments, metal binding compounds may be modified by attachment of radioligands to confer radioactivity that can be detected by means of PET scanning, autoradiography, and/or magnetic resonance imaging. Additionally, the amyloid-binding and metal probes described herein may be administered therapeutically to prevent protein aggregation.

EXAMPLE 3

Cytosolic β-amyloid Deposition in Alzheimer's Disease Lens

Postmortem eyes and brain specimens were obtained from AD and control patients and primary aqueous humor from non-AD volunteers undergoing cataract surgery. Dissected lenses where analyzed by slitlamp stereophotomicroscopy, Western blot, tryptic digest sequencing, anti-Aβ SELDI mass spectrometry, immunohistochemistry, and immunogold electron microscopy. Primary aqueous humor was analyzed by anti-Aβ SELDI mass spectrometry. Binding and aggregation studies were conducted to investigate Aβ-lens protein interactions.

Aβ1-40 and Aβ1-42 have both been identified in the human lens at concentrations comparable to brain and Aβ1-40 in primary aqueous humor at concentrations comparable to cerebrospinal fluid. Aβ accumulates in AD lenses as electron-dense deposits found exclusively in the cytoplasm of supranuclear/deep cortical lens fiber cells (n=4). Invariably, supranuclear but not nuclear cataracts were observed in AD (n=9) but not non-AD control lenses (n=9), these cataracts co-localized with enhanced Aβ immunoreactivity and birefringent Congo Red staining. Aβ binds αB-crystallin, an abundant cytosolic lens protein also expressed in some astroglia and neurons in AD brain. In vitro, Aβ promotes formation of lens protein aggregates that contain protofibrils and exhibit double Aβ/αB-crystallin immunoreactivity.

Thus, Aβ is present in the cytosol of lens fiber cells where this amyloidogenic peptide may promote regionally-specific lens protein aggregation and supranuclear cataract formation in AD. Evaluation of human tissue was carried out as follows.

Human Lens, Brain, and Aqueous Humor Specimens. Subject lenses were dissected from intact globes. All lens specimens used in this study were free of traumatic, morphological, or cold-storage artifacts. Comprehensive neuropathological examinations were conducted according to established procedures and assessed according to CERAD criteria (Mirra et al., Neurology 41(u):479-86 (1991)). Primary aqueous humor was obtained from non-AD patients undergoing routine cataract extraction. Samples of anterior chamber fluid were collected at the beginning of intraocular surgery with a sterile 0.5 cc tuberculin syringe and frozen at −80° C. until analysis.

Reagents. Human A: peptides were synthesized by tBOC chemistry and purified by chromatography on a preparative C-18 or C-4 RP-HPLC system. Lot purity (>98%) was assessed by mass spectrometry and composition by amino acid analysis. Purified recombinant human αB-crystallin, rabbit anti-human αB-crystallin polyclonal antibody and mouse anti-Aβ mAb WO2 (Aβ$_{5-8}$) were used to analyze eye tissues. Anti-Aβ mAbs 6E10 (Aβ1-17) and 4G8 (Aβ17-24) (Signet Laboratories, Dedham, Mass.), anti-Aβ mAβ-A$_4$ (Aβ$_{8-17}$, Dako, Carpenteria, Calif.) and anti-β-APP mAb 22C11 (N-terminal β-APPP66-81, Research Diagnostics, Flanders, N.J.) were purchased as purified IgG. Protein concentrations were determined by the bicinchoninic acid method (Pierce, Rockford, Ill.).

Slitlamp Stereophotomicroscopy and Lens Classification. Dissected lenses were bathed in 37° C. isotonic medium Tc-199 (Invitrogen, Carlsbad, Calif.), illuminated for slit-beam stereo photomicroscopy, and graded according to Cooperative Cataract Research Group criteria by an experienced rater blind to clinical history details and neuropathological diagnoses (Chylack, Ciba Found Symp. 106:3-24 (1984.))

β-APP Purification and Western Blot. Tissues were homogenized in ice-cold phosphate-buffered saline and ultracentrifuged (100,000×g, 1 hr, 4° C.). The pellet was retained as membrane extract. The salt concentration was adjusted to 350 mM NaCl (pH 8) and the extract applied to Macro-Q anion exchange resin (Pharmacia, Peapack, N.J.) according to a published protocol. (Moir et al., J. Biol. Chem. 273(9):5013-19 (1998)). Samples were eluted with 1 M NaCl in 50 mM Tris, pH 8.0, blotted, and probed for β-APP with mAb 6E10.

Human Lens Aβ Western Blots. Lyophilized lenses were homogenized in ice-cold phosphate-buffered saline and ultracentrifuged (100,000×g, 1 hr, 4° C.). Aliquots of the soluble and urea-resolubilized pellet fractions were electrophoresed on Tris/tricine-PAGE gels and western blotted. Aβ was detected with mouse anti-Aβ mAb WO2 (Aβ$_{5-8}$) and other antibodies and analyzed by densitometry. (Cherny et al., J. Biol. Chem. 274(33):23223-28 (1999)).

Tryptic Digest Sequencing/Electrospray Ionization Mass Spectrometry. Lens homogenate was prepared as described above and ultracentrifuged. The supernatant and urea-resolubilized pellet fractions were separately dissolved in sample buffer containing 8M urea, heated, electrophoresed on 10-20% Tricine gels, and stained with Coomassie Blue. A discretely staining ~4 kDa Coomassie-detectable band was excised, minced, and trypsinized.

Extracted peptides were fractionated by RP-HPLC and subjected to electrospray ionization and LCQ-DECA ion-trap mass spectrometry (ThermoFinnigan, San Jose, Calif.). Eluting peptides were isolated and fragmented to produce a tandem mass spectrum. Peptide sequences were identified by matching protein and translated nucleotide databases with the acquired fragmentation pattern (Sequest, ThermoFinnigan).

Anti-Aβ Surface-Enhanced Laser/Desormtion Ionization Mass Spectrometry (SELDI-MS). Human lens protein extracts or primary aqueous humor samples were incubated on a SELDI-MS protein array chip (Ciphergen Biosystems, Fremont, Calif.) pre-coated with mouse anti-Aβ mAb 4G8 or non-immune mouse IgG. Bound protein was detected by SELDI-MS time-of flight mass spectrometery. Calibration was conducted with synthetic human Aβ1-42 and Aβ1-40.

Anti-Aβ Immunohistochemistrv and Congo Red Staining. Lenses were fixed (0.5% glutaraldehyde, 2 hours; 4% paraformaldehyde, 2 days), embedded in paraffin, and sectioned at 8 μm. The tissue sections were stained with alkaline Congo Red and examined by brightfield and cross-polarizing light photomicroscopy or treated with 90% formic acid, immunostained with anti-Aβ mAb β A 4, and processed for conventional immunohistochemistry (Vectastain, Vector Laboratories, Burlingame, Calif.). Thioflavin-S staining was conducted on 8 μm paraffin-embedded sections using 1% Thioflavin-S, acetic acid (1%) differentiation, and fluorescence photomicroscopic detection.

Immunogold Electron Microscopy (IEM). Fixed lenses were cryosectioned and processed for immunogold electron microscopy. Mouse anti-Aβ mAbs (4G8 or 6E10) or anti-β-APP (22C11) were used for immunostaining. Protein aggregates and lens specimens assayed for double anti-β/anti-αB-crystallin immunogold analysis were spotted on carbon-coated hydrophilic grids, incubated with mAb 4G8 or non-immune mouse IgG, incubated with rabbit anti-mouse polyclonal antibody (Dako, Carpenteria, Calif.), and exposed to 15 nm gold-conjugated Protein-A (Jan Slot, Utrecht, Netherlands). Grids were fixed with 1% glutaraldehyde, quenched with glycine, incubated with anti-αB-crystallin polyclonal antibody or normal rabbit serum, and exposed to 10 nm gold-conjugated Protein-A. Due to the very high concentration of αB-crystallin relative to Aβ in the lens, the anti-αB crystallin antibody dilution was adjusted to maximize co-visualization of both proteins. To control for antibody specificity, primary antibodies (anti-Aβ mAb 4G8 and anti-αB-crystallin pAb) were pre-absorbed overnight at 4° C. with excess antigenic protein (i.e., synthetic human Aβ1-40 or recombinant human αB-crystallin, respectively) and briefly centrifuged before use. IEM specimens were negatively stained with uranyl acetate and examined on a JEOL 1200EX transmission electron microscope.

ELISA Binding Assay. Recombinant human αB-crystallin was incubated for 1 hr at 20° C. in 96-well microtiter plates pre-coated with synthetic human Aβ1-42, synthetic human Aβ1-40, or bovine serum albumin. Bound αB-crystallin was detected by incubation with a rabbit polyclonal antibody followed by anti-rabbit horseradish peroxidase conjugate and developed with 3,3',5,5'-tetramethylbenzidine dihydrochloride. (Moir et al., Biochemistry 38(14):4595-603 (1999)). Absorbance (λ450) was spectrophotometrically assessed (SpectraMax-Plus, Molecular Devices, Sunnyvale, Calif.) and blanked against wells without added αB-crystallin. Data points are means of triplicate measurements ±standard error.

In vitro Assays. Intact human lenses were homogenized in ice-cold, filter-sterilized analytical-grade HPLC water, ultracentrifuged (100,000×g, 1 hr, 4° C.), and the supernatant retained as soluble total lens protein (TLP). Synthetic human Aβ1-42 was ultrasonically solubilized in HPLC water and centrifuged to remove precipitated material. Incubation mixtures (Aβ1-42, 45 µg/ml (10 µM); TLP, 1 mg/ml) were prepared in sterile Chelex®-treated phosphate-buffered saline, pH 7.4, plated under sterile conditions in 96-well microtiter plates, sealed, and incubated in the dark for 7 days at 37° C.

Evaluation of Lens Tissue

Figure 1A:
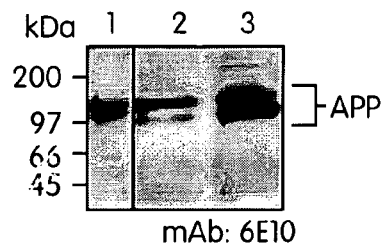
FIG. 1A is a β-APP western blot (mAb 6E10) of human brain (lane 1), lens (lane 2), and retina (lane 3) after anion exchange concentration and purification.
Figure 1B:
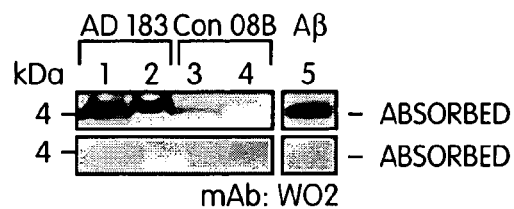
FIG. 1B is a Western blot of AD and non-AD control lens homogenate probed with anti-Aβ mAb WO2 (top) or anti-Aβ mAb WO2 pre-absorbed with excess synthetic human Aβ 1-40 (bottom {Lane 1,3: supernatant. Lanes 2,4: urea-resolubilized pellet. Lane 5: synthetic human Aβ1-40 (0.5 ng)}.

The identification and characterization of β-APP and Aβ in the adult human lens is shown in FIG. 1. β-APP was purified and concentrated from lens homogenate by anion exchange absorption and detected full length β-APP (110 kDa and 130 kDa) by western blot utilizing mAb 6E 10 (FIG. 1A). Full length β-APP was detected by western blot in the B3 human lens epithelial cell line and primary human lens epithelial cells using other anti-β-APP antibodies directed against the C-terminal (C8, A8717) and N-terminal (22C11) β-APP domains. Western blot with the anti-Aβ mAb WO2 (Aβ5-8) revealed an Aβ-immunoreactive band that migrated at a molecular weight equivalent to apparent monomeric Aβ (~4 kDa) that was detectable in both the supernatant and urea-resolubilized pellet fractions obtained from human lens protein homogenate (FIG. 1B). This band was not detected when blots were probed with mAb WO2 pre-absorbed with synthetic Aβ. (FIG. 1B, lower panel) or with a polyclonal antibody (pAb-369) directed against the C-terminal domain of β-APP. A small sampling of lenses examined by anti-Aβ quantitative western blot densitometry revealed a trend towards increased total monomeric Aβ load in AD (total monomeric Aβ: 3.01, 0.4, 6.17 µg/g protein) relative to age-matched non-AD (0.52, 0.98, 0.53 µg/g protein) when assayed on the same blot. These Aβ tissue concentrations are comparable to those determined for human brain using identical methods. (McLean et al., Ann. Neurol. 46(6):860-66 (1999)). Due to the anatomically circumscribed accumulation of Aβ within the lens (see below), this quantitative analysis likely to have underestimated the local Aβ tissue concentration in the supranuclear lens subregion. A more extensive quantitative Aβ analysis conducted on microdissected lenses specimens is currently underway.

Figure 1C:
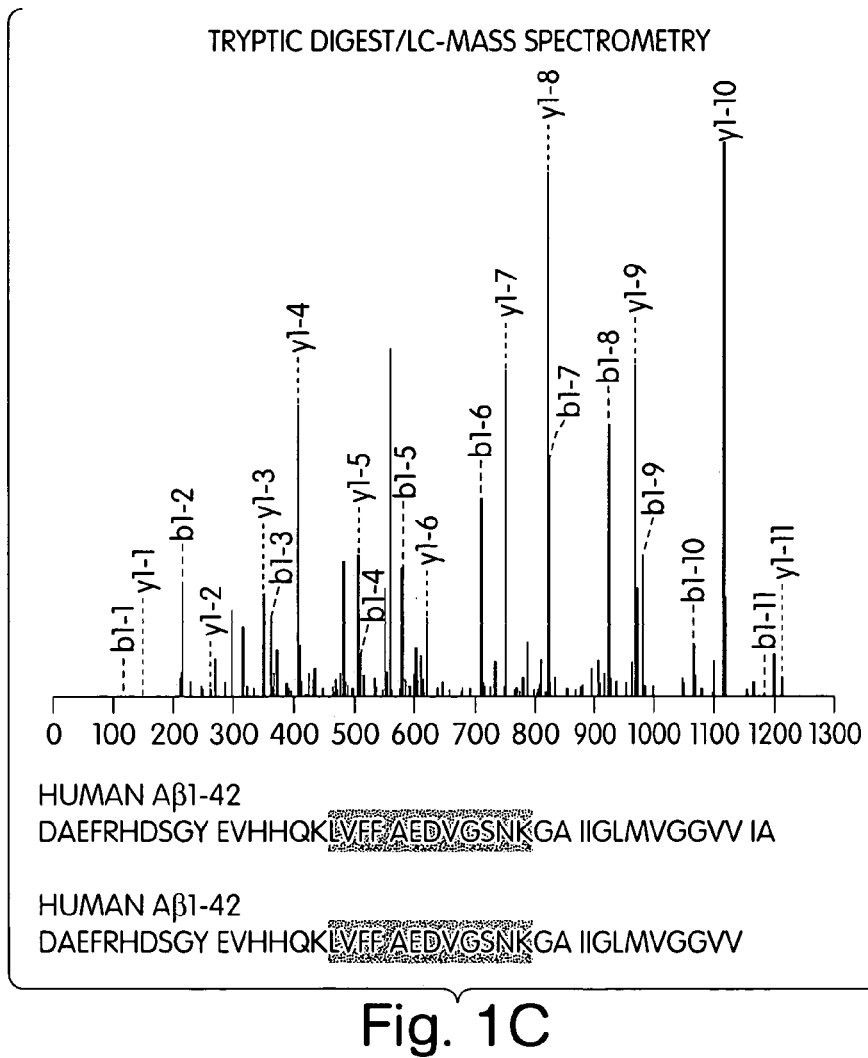
FIG. 1C shows the identification of Aβ in AD lens homogenate by tryptic digest sequencing/ tandem LC-mass spectrometry. Donor lens was obtained from an 83 y.o. male with severe AD. The ~4 kDa Coomassie-stained band from SDS-PAGE analysis of the lens protein extract yielded a unique tryptic digest peptide fragment that corresponded to the Aβ region of β-APP (residues 688-699). The identifying tryptic fragment is highlighted by the black box overlying the human Aβ sequences.
Figure 1D:
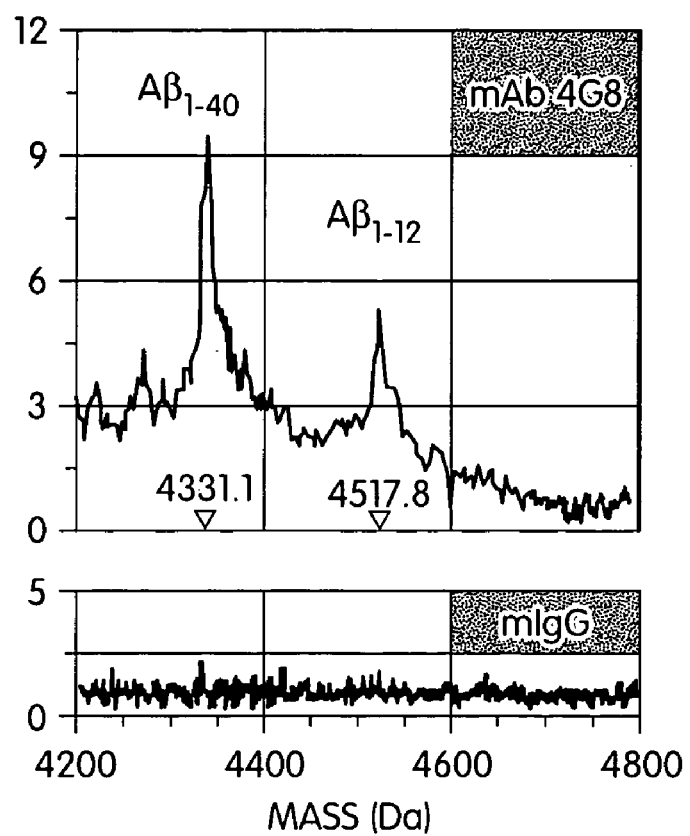
FIG. 1D shows the confirmation of monomeric Aβ1-42 and Aβ1-40 in adult human lens protein extract analyzed by anti-Aβ SELDI-MS. Donor lens was obtained from a 56 y.o. female without AD. Capture antibodies, mouse anti-Aβ mAb 4G8 (top panel) or non-immune mouse IgG (bottom panel). Mass ratio of monomeric Aβ1-40 to Aβ1-42 in the soluble lens protein fraction is ~5:1. The two A monomer peaks detected in the human lens protein extract were identical to those obtained with synthetic human Aβ1-40 and Aβ1-42. A similar spectrogram detected Aβ1-40 in human primary aqueous humor.

The identity of Aβ in human lens was confirmed by tryptic digestion sequencing using electrospray ionization LC-mass spectrometry (FIG. 1C). The ~4 kDa band observed on anti-Aβ western blot of lens extract obtained from an 83 y.o. male donor with severe AD was excised and sequenced. This analysis yielded a 12-residue tryptic peptide (LVFFAEDVGSNK (SEQ ID NO:1), m.w. 1326.49) with two charge states, +2 and +1, that uniquely identified an internal peptide within the Aβ region of β-APP β-APP$_{688-699}$). The amino acid sequence of this tryptic peptide is identical in both Aβ1-40 and Aβ1-42 (FIG. 1C). In order to distinguish these two Aβ isoforms, surface-enhanced laser desorption ionization mass spectrometry (SELDI-MS) was performed on human lens extract obtained from a 56 y.o. non-AD female. When the protein chip array was pre-coated with the mouse anti-Aβ mAb 4G8 (FIG. 1D, upper panel), two major peaks were detected that corresponded to human Aβ1-40 (observed m.w. 4331.1 kDa; predicted m.w. 4329.9 kDa) and Aβ1-42 (observed m.w. 4517.8 kDa; predicted m.w. 4514.1 kDa) in a relative mass ratio of ~5:1, respectively. Signals were not observed when array wells were pre-coated with non-immune mouse IgG (FIG. 1D, lower panel) or without capture antibody. The detected peaks were identical to those obtained with synthetic human Aβ1-40 and Aβ1-42 and in lens protein extracts spiked with synthetic human Aβ. Anti-Aβ SELDI-MS analyses of adult human primary aqueous humor obtained during cataract surgery from three non-AD patients yielded a large peak that corresponded to human Aβ1-40 (12.5+2.1 ng/ml) and a minor peak near the assay detection limit that corresponded to Aβ1-42.

These findings encouraged the conduction of slitlamp survey of human lenses obtained from nine donors with confirmed AD neuropathology (5 females, 4 males; mean age 81.8+11.2 years; mean post-mortem interval, ~8 hours) and eight non-AD control donors (frontotemporal dementia, n=2; progressive supranuclear palsy, n=1; diffuse Lewy body disease (with minimal amyloid pathology), n=1; aged donors without neurological disease, n=3; and one 14 year old male donor. Supranuclear cataracts (FIGS. 2A and 2B), an uncommon phenotype (Chylack et al., Invest. Ophthalmol Vis Sci 25(2):166-73 (1984), were observed in all nine AD cases but in none of the controls. These cataracts were typically concentrated in the equatorial region, and, in some cases, extended into the deep cortical areas. Variation in the extent of opacification, cataract morphology, and presence of co-morbid lens pathology was observed. The possibility that the observed cataracts were artifacts was excluded, since no lens swelling, diffuse cloudiness, or other global changes that would indicate organ damage, and postmortem lens changes do not result in focal lens opacification were observed.

Histological and ultrastructural analyses were performed to localize Aβ in lenses obtained from age-matched AD (n=4) and non-AD (n=4) donors. Aβ lens exhibited Aβ immunostaining in the cortical and supranuclear lens subregions (FIG. 2C). Congo Red staining was observed (FIG. 2D) that demonstrated dichrosim and green-red birefringence, when viewed under strong cross-polarized light (FIG. 2E), tinctorial properties that are pathognomonic of amyloid. This birefringent Congo Red staining was observed in the same regions that demonstrated Aβ immunostaining. Minor Congo Red staining was noted in the lens capsule that did not exhibit Aβ immunostaining and thus appeared to be artifact. Intense Thioflavin-S fluorescence was also observed in the same supranuclear and deep cortical lens regions in which Aβ immunoreactivity and birefringent Congo Red staining was detected. Examination of aged, non-AD lens revealed faint Aβ immunoreactivity (FIG. 2F) in the supranuclear and deep cortical lens regions. The superficial cortical regions in control lens demonstrated congophilia (FIG. 2G) with minimal birefringence (FIG. 2H). In the AD specimens, those lens regions exhibiting strong Aβ immunoreactivity and Congo Red staining corresponded to the same areas in which cataracts were identified by slitlamp examination (FIG. 2I).

Figure 2J:
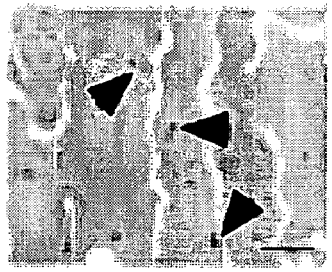
FIGS. 2J-O show the ultrastructural characterization of cytosolic Aβ immunoreactivity in representative human lenses.
Figure 2K:
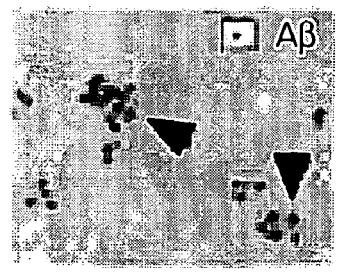
Figure 2L:
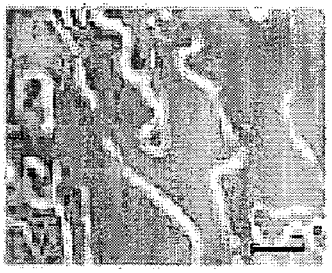
Figure 2M:
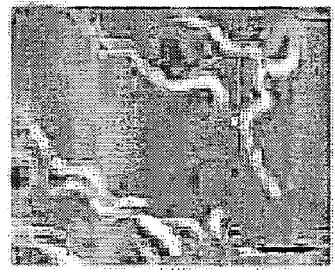
Figure 2N:

Analysis of AD lens specimens (n=4) by anti-Aβ (mAb 4G8) immunogold electron microscopy (IEM) revealed abundant clusters of electron-dense Aβ immunoreactive aggregates that localized exclusively to the lens fiber cell cytoplasm (FIGS. 2J and 2K). Aβ immunoreactivity was not observed in classical fibrillar structures, extracellular regions, membrane-associated material, or the lens epithelium. Age-related sclerosis prevented investigation of the lens nucleus. Minimal Aβ immunoreactivity was deleted in aged, non-AD human lens fiber cells (FIG. 2L), and Aβ immunoreactivity was not observed in a lens from a normal 14-year old male or in the B3 human lens epithelial cell line. Pre-absorption of the antibody with excess synthetic human Aβ (FIG. 2M) or exclusion of the primary anti-Aβ antibody abolished immunostaining in AD lens sections. Sections probed with the anti-β-APP mAb 22C11 (FIG. 2N), non-immune antibody, or secondary antibody alone similarly did not exhibit anti-Aβ immunoreactivity.

Mature lens fiber cells contain the highest protein concentration in the body (>300 mg/g). These terminally differentiated post-mitotic cells neither synthesize new protein nor efficiently clear denatured protein. Once expressed, cytosolic lens structural proteins persist for life and are continuously challenged by photo-oxidation. These factors cumulatively foster progressive accumulation of insoluble intracellular protein aggregates. The cytosolic localization of the potent pro-aggregant Aβ within the same subcellular compartment as the highly-concentrated lens structural proteins suggested that Aβ might induce protein aggregation within the lens fiber cell cytoplasm. Some of the Aβ-immunoreactive deposits detected might co-aggregate with other cytosolic lens proteins such as αB-crystallin.

Figure 2O:
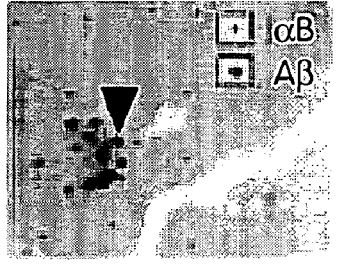
Figure 3A:
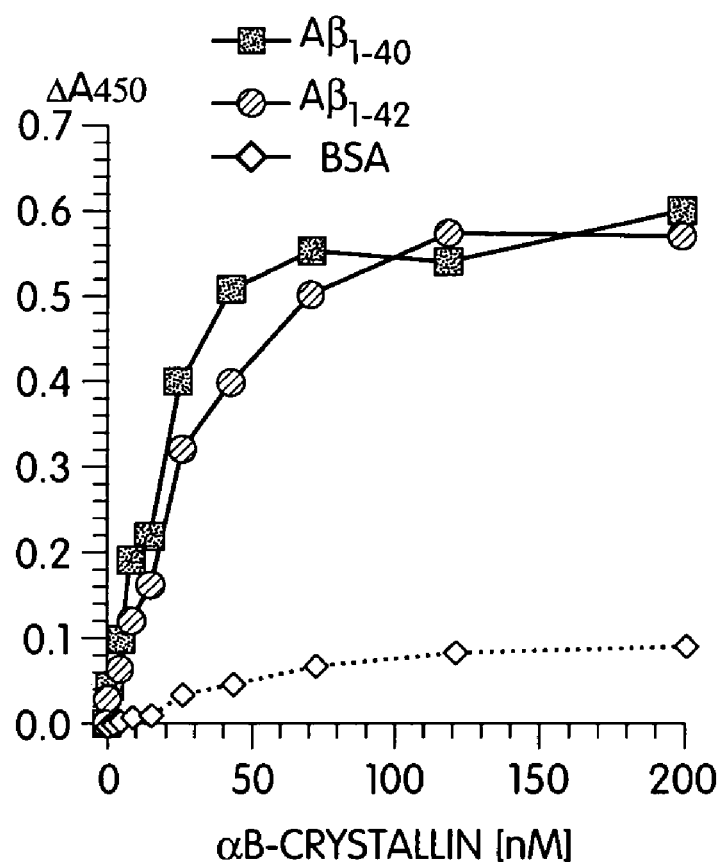
FIG. 3A shows the binding of increasing concentrations of recombinant human αB-crystallin to immobilized synthetic human Aβ1-42, synthetic human Aβ1-40, or bovine serum albumin (BSA) after 1 hour incubation.
Figure 3B:
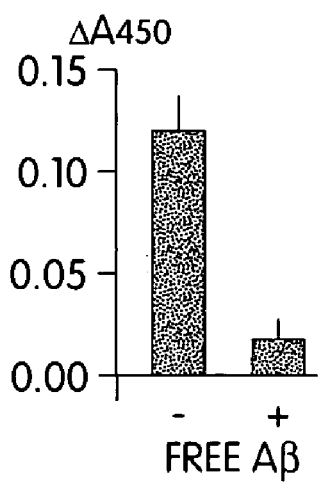
FIG. 3B shows the competition of binding by addition of excess free Aβ.
Figure 3C:
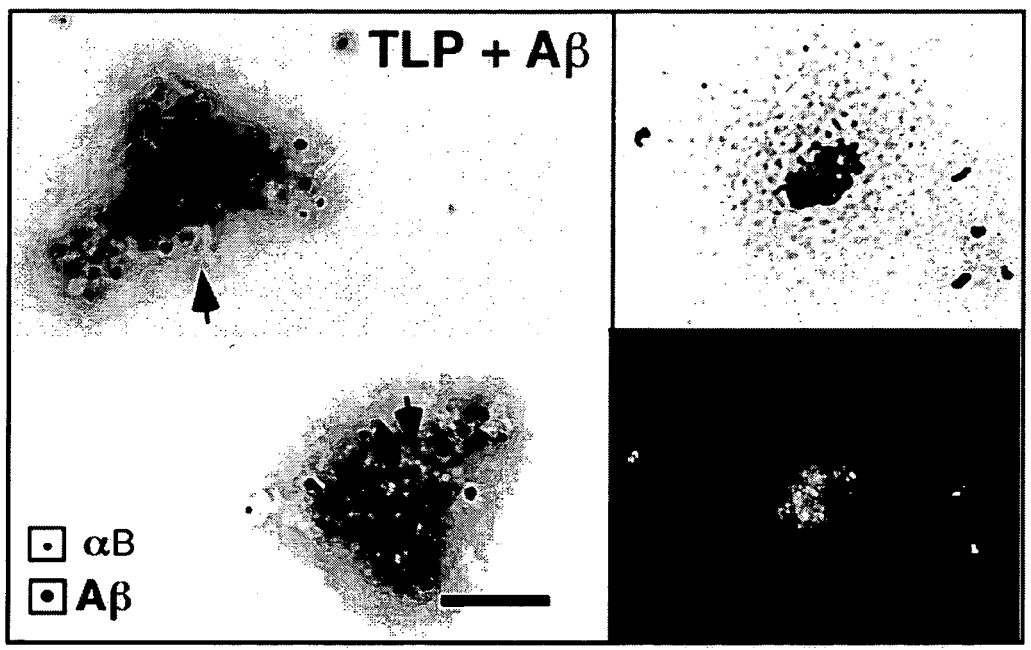
FIG. 3C shows that Aβ and αB-crystallin co-aggregate after 7 days incubation in vitro. Human soluble lens protein extract (TLP, 1 mg/ml) co-incubated with synthetic human Aβ1-42 (45 µg/ml, 10 µM) for 7 days and examined by anti-Aβ/anti-αB-crystallin double IEM. Larger gold particles (15 nm diameter) detect Aβ immunoreactivity. Smaller gold particles (10 nm diameter) detect anti-αB-crystallin immunoreactivity. Black arrows indicate curvilinear protofibril structures within electron-dense amorphous aggregates. Also shown are precipitated aggregates stained with Congo Red and viewed by brightfield (top inset) or strong cross-polarized light (bottom inset) illumination.
Figure 3D:
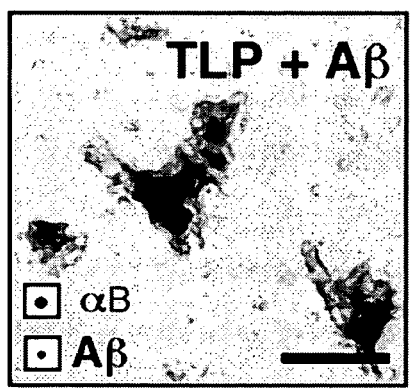
FIG. 3D shows TLP co-incubated with synthetic human Aβ1-42 and examined by anti-Aβ/anti-αB-crystallin double IEM using primary antibodies pre-absorbed with excess synthetic human Aβ1-40 and purified recombinant human αB-crystallin.
Figure 3E:
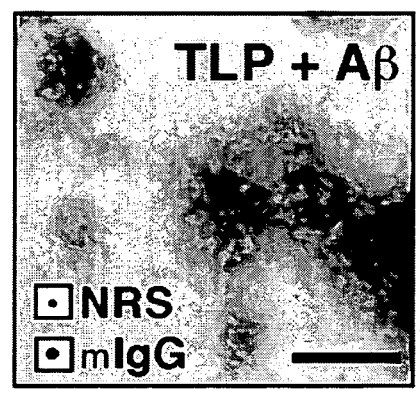
FIG. 3E shows TLP co-incubated with synthetic human Aβ1-42 and assayed with non-immune mouse IgG and rabbit serum.
Figure 3F:
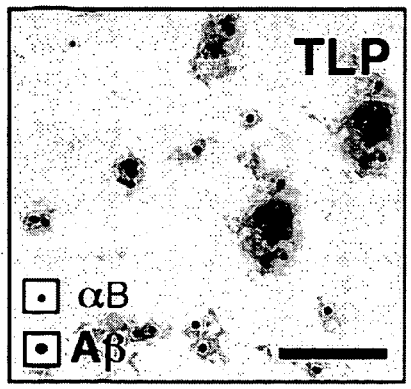
FIG. 3F shows TLP incubated without Aβ and assayed as in FIG. 3C. Also shown is synthetic human Aβ1-42 incubated without TLP and assayed as in FIG. 3C.
Figure 3G:
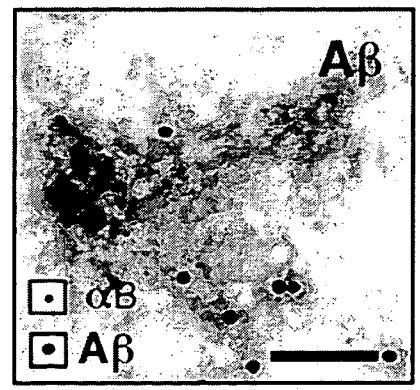
As shown in FIG. 3G, Aβ incubated alone revealed only single-label immunostaining for AB. The insert boxes in the figures illustrate gold particle size (to scale) in the micrograph. Scale bars=100 nm.
Figure 4:
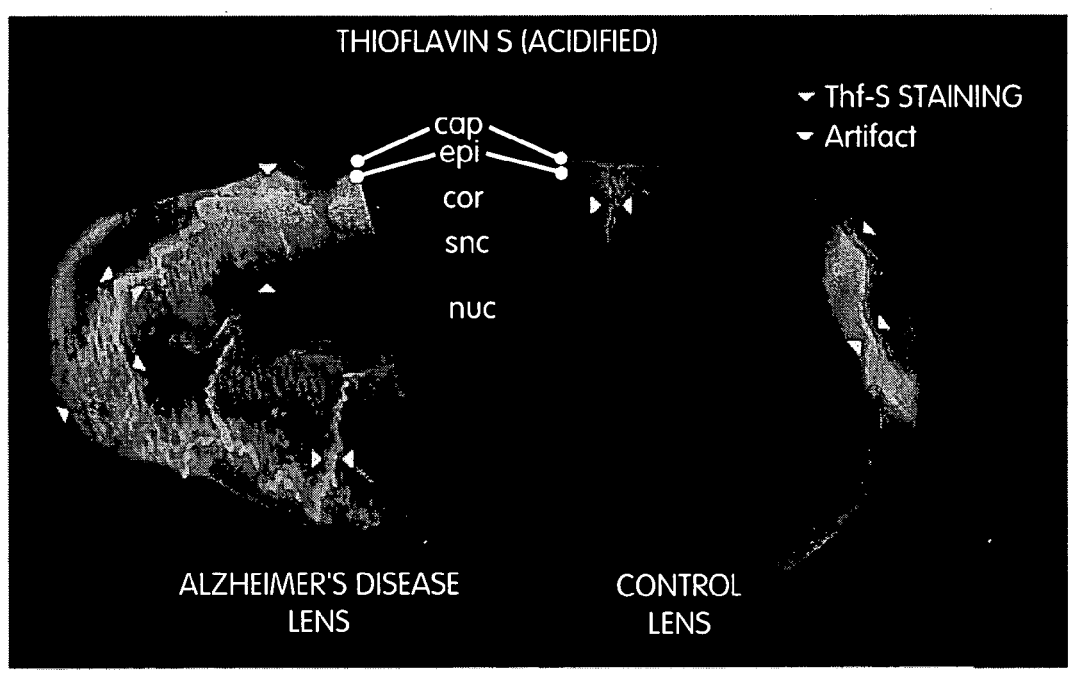
FIG. 4 is a photograph showing increased lens protein thioflavin fluorescence mediated by Aβ in an Alzheimer's Disease lens compared to a normal control lens.

Electron-dense cytosolic aggregates were detected that exhibited both Aβ and αB-crystallin immunoreactivity (FIG. 2O), which prompted the investigation of the interaction of Aβ with αB-crystallin in vitro. A modified ELISA was used to study the binding of synthetic human Aβ1-42 and Aβ1-40 to recombinant human αB-crystallin. Brief (1 hr) incubation of increasing concentrations of αB-crystallin with immobilized Aβ1-42 or Aβ1-40 resulted in saturable, high-affinity binding (Kapp, ~20 nM, FIG. 3A) that was competitively inhibited by addition of excess soluble Aβ (FIG. 3B). This binding and the potent pro-oxidant properties of the Aβ peptide could, over time, promote lens protein aggregation within the fiber cell cytosol. This was further investigated by incubating human total lens protein (TLP) extract with synthetic human Aβ1-42 for 7 days and analyzing the resulting mixtures by anti-Aβ/anti-αB-crystallin double IEM. Formation of electron-dense aggregates (FIG. 3C, left panel) were observed that were similar to those detected in the ex vivo AD lens specimens. Single aggregates demonstrated both Aβ and αB-crystallin immunoreactivity, as well as birefringent Congo Red staining (FIG. 3C, right panels) and increased thioflavin-S fluorescence. These aggregates also demonstrated curvilinear protofibril (See Hartley et al., N. Neurosci 19(20):8876-84 (1999) but not classical Aβ fibril structures. Double IEM analysis using primary antibodies (anti-Aβ mAb 4G8 and anti-αB-crystallin pAb) pre-absorbed with excess synthetic human Aβ1-40 and recombinant human αB-crystallin (FIG. 3D), or control non-immune mouse IgG and normal rabbit serum (FIG. 3E) did not result in immunogold staining, suggesting that these results were not due to non-specific staining artifact. TLP (FIG. 3F) or Aβ (FIG. 3G) incubated alone revealed only single-label immunostaining for a αB-crystallin or AB, respectively.

Increased Accumulation of Aβ Peptides in Eye Tissue of Alzheimers Patients Compared to Normal Control Eye Tissue Aβ1-42 and Aβ1-40 have been identified in the human lens and Aβ-40 in primary human aqueous humor at concentrations comparable to aged human cerebral cortex and cerebrospinal fluid, respectively. Increased deposition of electron-dense Aβ-immunoreactive aggregates has also been observed within lens fiber cell cytoplasm in the supranuclear subregion of AD lenses. The cytosolic localization of lenticular Aβ is significant since this amyloidogenic protein is in direct proximity to the highly concentrated protein milieu within the lens fiber cell and is thus positioned to foster lens protein aggregation. This is supported by evidence from double immunogold electron microscopic examination of AD lenses showing Aβ- and αB-crystallin immunoreactivity within single cytosolic aggregates and in vitro studies demonstrating high-affinity binding and co-aggregation of Aβ and αB-crystallin.

Although previous investigators have observed Aβ within other intracellular compartments, the finding of this peptide in the cytoplasm proper was unexpected. The cytosolic localization of Aβ in the lens results from liberation of this peptide from other intracellular compartments during lens epithelial cell terminal differentiation as these cells mature into the long-lived, post-mitotic lens fiber cells. During this process, epithelial cells on the anterior surface of the lens migrate to the equatorial germinative zone and there undergo morphological elongation, nuclear and organellar disintegration, and cessation of protein synthesis. β-APP and its metabolic products, including Aβ, are initially contained within organelles involved in β-APP processing (i.e., endoplasmic reticulum, Golgi apparatus and trans-Golgi network). As these organelles disintegrate during terminal differentiation, Aβ is liberated into the cytosol. Alternatively, endocytic Aβ re-internalization, a clearance pathway, also plays a role in the cystolic localization. This latter mechanism is consistent with the presence of Aβ in primary aqueous humor.

These findings provide evidence for extracerebral AD-associated pathology. Specifically, apparent Aβ-related pathology has been observed in the equatorial supranuclear and deep cortical subregions of AD lenses. Cataracts in these peripheral lens subregion are obscured from inspection by the iris and are neither apparent on routine medical examination nor associated with visual impairment. Aβ-immunoreactive cytosolic microaggregates in the cytoplasm of supranuclear lens fiber cells and cataract formation in the same lens subregion are both indicative of neuropathology. Within the lens fiber cell cytoplasm, electron-dense aggregates such as those observed in the AD lenses represent sharp discontinuities in the local refractive index. Small refractive index fluctuations result in very large increases in local light scattering, and Aβ-mediated lens protein aggregation contributed to the increased light scattering that was detected as supranuclear cataracts in the AD lens specimens. The longevity of expressed protein in the lens, the relatively inefficient protein turnover capacity of mature lens fiber cells, and the optical accessibility of the lens from the periphery indicate that Aβ deposition in the lens leads to regionally-specific lens protein aggregation, which is detectable throughout the course of AD, and, therefore, provides a sensitive and valuable tool by which to detect and monitor progression of a neuropathological condition.

EXAMPLE 4

Detection of Amyloidogenic Disorders in Human and Veterinary Patients

Fluorophotometric or other imaging techniques to diagnose AD or other amyloidogenic disorders are easily carried out in a doctor's office, clinic or hospital setting. The methods are useful to assess patients for AD or related disorders including: AD, Familial AD, Sporadic AD, Creutzfeld-Jakob disease, variant Creutzfeld-Jakob disease, spongiform encephalopathies, Prion diseases (including scrapie, bovine spongiform encephalopathy, and other veterinary prionopathies), Parkinson's disease, Huntington's disease (and trinucleotide repeat diseases), amyotrophic lateral sclerosis, Down's Syndrome (Trisomy 21), Pick's Disease (Frontotemporal Dementia), Lewy Body Disease, neurodegenration with brain iron accumulation (Hallervorden-Spatz Disease), synucleinopathies (including Parkinson's dieseae, multiple system atrophy, dementia with Lewy Bodies, and others), neuronal intranuclear inclusion disease, tauopathies (including progressive supranuclear palsy, Pick's disease, corticobasal degeneration, hereditary frontotemporal dementia [with or without parkisonism], Guam amyotrophic lateral sclerosis/parkinsonism dementia complex). These disorders may occur alone or in various combinations. Patients to be tested include those suspected of suffering from such disorders or who are at risk of developing such disorders. For example, patients with a family history of AD or other risk factors such as advanced age are tested using the techniques described herein.

The operator uses an light detection instrument to non-invasively and accurately ascertain the nature of protein aggregation in one or both eyes. The light is directed to target the ocular lens. However, since the amyloid proteins are also expressed in the cornea and elsewhere in the eye, other structures such as the cornea, the vitreous or aqueous humor, or other ocular constituents and components are targeted. The output from the device is a series of numbers which may be composited using the assistance of a computer. The number(s) are either within a normal range or outside a normal range and are compared to normed population data using this instrument in diseased and normal patient populations. This number or series of numbers is compared to prior measurements using this or similar devices and is assessed within the context of other clinical information. The use of this device is thus of aid in the diagnosis, prognosis, and monitoring of AD and related disorders. This information is useful to the patient, the patient's family, the assessing clinician, and other care providers, to determine future therapeutic strategies. The use of the device is also helpful in the staging of disease (e.g., pre-clinical, early, middle, late, etc.).

The methods and instrumentation is useful for monitoring the effectiveness of various treatments for AD and related disorders. For example, a decrease in the amount or a decline in the rate of formation of $A\beta$ itself or $A\beta$-associated aggregates in eye tissue over time indicates improvement of AD or a related condition, e.g., as a result of successful therapeutic intervention.

Other embodiments are within the following claims.

What is claimed is:

1. A method of diagnosing Alzheimer's Disease or a predisposition thereto in a mammal, the method comprising
    a) contacting an ocular tissue with a detectably-labeled compound that preferentially binds to an amyloid protein located in an ocular tissue, wherein the detectably-labeled compound is an amyloidophilic fluorescent dye;
    b) allowing said compound to distribute into the lens; and
    c) imaging said ocular tissue,
wherein an increase in binding of said compound to said ocular tissue compared to a normal control level of binding indicates that said mammal is suffering from or is at risk of developing Alzheimer's Disease.

2. The method of claim 1, wherein said detectably-labeled compound is thioflavin S.

3. The method of claim 1, wherein said detectably-labeled compound is thioflavin T.

4. The method of claim 1, wherein said detectably-labeled compound preferentially binds to an amyloid-$\beta$ (A$\beta$) polypeptide.

5. The method of claim 4, wherein said detectably-labeled compound preferentially binds to A$\beta$ (1-42).

6. The method of claim 1, wherein the ocular tissue comprises a cortical region of the eye lens.

7. The method of claim 6, wherein the ocular tissue comprises a supranuclear region of an eye lens.

8. The method of claim 1, wherein said increase is at least 10% greater than said normal control value.

9. The method of claim 1, wherein said increase is at least 25% greater than said normal control value.

10. The method of claim 1, wherein said increase is at least 50% greater than said normal control value.

11. The method of claim 1, wherein said increase is at least 100% greater than said normal control value.

* * * * *